(12) United States Patent
Geromanos et al.

(10) Patent No.: US 8,193,485 B2
(45) Date of Patent: Jun. 5, 2012

(54) METHOD AND APPARATUS FOR IDENTIFYING PROTEINS IN MIXTURES

(75) Inventors: Scott J. Geromanos, Middletown, NJ (US); Marc Victor Gorenstein, Needham, MA (US); Jeffrey Cruz Silva, Beverly, MA (US); Guo-Zhong Li, Westborough, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 12/908,235

(22) Filed: Oct. 20, 2010

(65) Prior Publication Data

US 2011/0260049 A1    Oct. 27, 2011

Related U.S. Application Data

(63) Continuation of application No. 11/596,756, filed as application No. PCT/US2005/017742 on May 20, 2005, now Pat. No. 7,851,742.

(60) Provisional application No. 60/572,532, filed on May 20, 2004.

(51) Int. Cl.
*H01J 49/00* (2006.01)
*B01D 59/44* (2006.01)

(52) U.S. Cl. ......... 250/282; 250/281; 250/284; 250/288

(58) Field of Classification Search .................. 250/281, 250/282, 284, 288
See application file for complete search history.

(56) References Cited

U.S. PATENT DOCUMENTS 5,672,869 A    9/1997    Windig et al.
(Continued)

FOREIGN PATENT DOCUMENTS

JP    08-334493 A    12/1996
(Continued)

OTHER PUBLICATIONS

Kerns, Edward H., et al., Buspirone metabolite structure profile using a standard liquid chromatographic-mass spectrometric protocol, Journal of Chromatography B, 1997, vol. 698, No. ½, pp. 133-145.

(Continued)

*Primary Examiner* — David A Vanore
(74) *Attorney, Agent, or Firm* — Muirhead and Saturnelli, LLC

(57) ABSTRACT

Protein identification in a complex sample begins by selecting a database having proteins likely to be in the sample. In-silico digestion is performed and a target peptide is selected from produced peptides. The masses of the Y- and B-ion fragments of the target peptide are determined. These masses are used to search previously obtained low- and high-energy AMRTs obtained from LC/MS analysis of the complex sample for masses on the list. Any mass observed in the data within a detection threshold are considered a hit. If enough hits accumulate in a given retention time, the target peptide is identified as being in the sample. The list of peptides identified in the complex sample can be used to identify the proteins present in the sample, track the chromatographic retention times of peptides between samples, and quantitate the peptides and proteins present in complex samples.

20 Claims, 25 Drawing Sheets

U.S. PATENT DOCUMENTS

| | | | |
|---|---|---|---|
| 6,613,508 | B1 | 9/2003 | Ness et al. |
| 6,717,130 | B2 | 4/2004 | Bateman et al. |
| 6,949,347 | B2 | 9/2005 | Singh et al. |
| 6,982,414 | B2 | 1/2006 | Bateman et al. |
| 7,052,846 | B2 | 5/2006 | Van Ness et al. |
| 7,052,915 | B2 | 5/2006 | Aebersold et al. |
| 7,112,784 | B2 | 9/2006 | Bateman et al. |
| 7,217,531 | B2 | 5/2007 | Singh et al. |
| 7,402,397 | B2 | 7/2008 | Chan-Hui et al. |
| 7,582,455 | B2 | 9/2009 | Brazeau et al. |
| 2003/0153007 | A1 | 8/2003 | Chen et al. |
| 2003/0186326 | A1 | 10/2003 | Regnier et al. |
| 2005/0092910 | A1 | 5/2005 | Geromanos et al. |

FOREIGN PATENT DOCUMENTS

| | | |
|---|---|---|
| JP | 2002-110081 A | 4/2002 |
| JP | 2004-503792 A | 2/2004 |
| WO | 02072863 | 9/2002 |
| WO | WO 2004/019035 A2 | 3/2004 |

OTHER PUBLICATIONS

Pelander, Anna, et al., Toxicological Screening with Formula-Based Metabolite Identification by Liquid Chromatography/Time-of-Flight Mass Spectrometry, Anal. Chem., 2003, vol. 75, No. 21, pp. 5710-5718.

Japanese Office Action dated Nov. 9, 2010.

Upslope inflection point 606a / Down slope inflection point 606b
Apex 604

METHOD AND APPARATUS FOR IDENTIFYING PROTEINS IN MIXTURES

This application is a continuation of U.S. application Ser. No. 11/596,756, filed Aug. 8, 2007 now U.S. Pat. No. 7,851,742, which is the National Stage of International Application No. PCT/US2005/17742, filed May 20, 2005, which claims the benefit of U.S. Provisional Application No. 60/572,532, filed May 20, 2004, all of which are hereby incorporated by reference.

BACKGROUND

1. Field of the Invention

The present invention relates generally to proteomics. More specifically, the present invention relates to using liquid chromatography in combination with mass spectrometry to identify and to quantify proteins, and peptides in a complex mixture, as well as to identify and quantify molecules in a complex mixture that produce precursor and fragment ions in a mass spectrometer. Further, the present invention also relates to using liquid chromatography in combination with mass spectrometry to retention-time track peptides in a complex mixture. More importantly the present invention provides a method of peptide identification without requiring the presence of a precursor ion mass thereby enabling the method to identify both chemically and post-translationally modified versions of peptides, allelic differences, peptides containing point mutations, as well as any other modifications of sequences deposited in the database being queried.

2. Background of the Invention

Proteomics generally refers to studies involving complex mixtures of proteins. The field of proteomics includes studying and cataloging proteins in biological systems. Proteomic studies typically focus on identification of proteins, determination of changes in relative abundance among different conditions, or both. Identification and quantification of proteins in complex biological samples is a fundamental problem in proteomics.

Liquid chromatography coupled with mass spectrometry (LC/MS) has become a fundamental tool in proteomic studies. Separation of intact proteins or of their proteolyzed peptide products by liquid chromatography (LC) and subsequent analysis by mass spectrometry (MS) forms the basis of many common proteomic methodologies. Methods that measure changes in the expression level of proteins are of great interest as they can form the basis of biomarker discovery and clinical diagnostics.

In conventional proteomic studies, proteins of interest typically are first digested to produce a specific set of proteolytic peptides rather than studying the intact proteins directly. The resulting peptides are then characterized during the proteomic analysis. A common enzyme used for such digestion is trypsin. In tryptic digestion, the proteins present in the complex mixture are cleaved to produce peptides as determined by the cleavage specificity of the proteolytic enzyme. From the identity and concentration of the observed peptides, algorithms known in the art can infer the identity and the concentration of the parent proteins.

In LC/MS analysis, the peptide digest is separated and analyzed by on-line, liquid chromatographic (LC) separation followed by on-line mass spectrometric (MS) analysis. Ideally, the mass of a single peptide, measured with sufficient accuracy, is sufficient to uniquely identity the peptide. In practice, however, achieved mass accuracies typically are on the order of 10 ppm or larger. In general, such mass accuracy is not sufficient to uniquely identify a peptide based upon mass measurement alone. For example, in the case of a mass accuracy of 10 ppm, on the order of 10 peptide sequences are identified in typical database searches. This number of sequences would increase significantly if search restraints on mass accuracy were lowered to allow for chemical or post-translational modifications, losses of H2O or NH3, point mutations, etc. Sequence repositories typically contain translated DNA sequences that have been annotated by homology to a known substrate. Thus, if a peptide's sequence is modified by either a deletions or substitutions, then tentative identification to that peptide by precursor mass only must be false.

Furthermore, two peptides can have the same amino acid composition but have different sequences. Mass accuracy alone is not sufficient to distinguish between peptides that differ in sequence but not in composition. Fragmentation techniques are known that cause peptides to break into fragments ions. These fragments can correspond to a subsequence of the original peptide, but other types of fragment ions may be observed. Fragment masses seen in the data can be used to confirm or deduce the precursor's sequence.

In the case of peptide precursors, subsequences can arise by the fragmentation at a single peptide bond in the precursor. Such fragmentation results in two sub-sequences. The fragment containing the peptide's C-terminal, if ionized, is termed a Y-ion, and the fragment containing the peptide's N-terminal, if ionized is termed a B-ion.

Known protein identification techniques search databases using accurate mass retention time (AMRT) data of precursors and fragments obtained from LC/MS experiments. For example, one way of obtaining such data is described in U.S. Pat. No. 6,717,130 to Bateman ("Bateman"), which is hereby incorporated by reference in its entirety. In Bateman, such data can be obtained using a high- and low-energy switching protocol applied as part of an LC/MS analysis of a single injection of a peptide mixture. In such data the low-energy spectra contains ions primarily from unfragmented precursors, while the high-energy spectra contain ions primarily from fragmented precursors.

To identify the presence of a protein in such data, an AMRT (empirically describing those ions from a peptide or from a fragment) is selected from the low-energy data. If trypsin is used in the digest, this AMRT is presumed to be a tryptic precursor. Using the AMRT data, known methods search a database of peptide masses for tryptic peptides whose masses lay within a mass search window or threshold.

If a theoretical peptide mass from a database lies within a mass search window of the mass of a precursor measured in the data, it is deemed a hit. That is, the precursor in the data is hit by the peptide in the database; or alternatively the peptide in the database is hit by the precursor in the data.

The search results in a hit-list of possible matching peptides from the database. These possible matching database peptides may or may not be weighted by statistical factors. The possible outcomes of such a search are that no possible matching database peptides are identified, one possible matching database peptide is identified, or more than one possible matching database peptide are identified. The higher the resolution of the MS, assuming proper instrument calibration, the smaller the ppm threshold, and consequently, the fewer the false identifications.

If there is one or more hit to the theoretical peptides in the database, conventional searches then use data from high-energy AMRTs to validate a possible matching database peptide. High-energy AMRTs are first searched to isolate those high-energy AMRTs that occur at the same retention time as the low-energy AMRT being validated. Typically, the high-energy AMRTs that are isolated are those whose retention times are substantially the same as the retention time of the low-energy AMRT being validated.

For each database peptide on the hit list, the algorithm determines the masses of all possible Y-ions and B-ions that can be obtained through collisionally induced disassociation of the precursor. The isolated high-energy AMRT data is then searched for each of these Y- and B-ions. The peptide sequence having the greatest number of hits, or satisfying other criteria, is returned as the correct hit, i.e., the identity of the target precursor. This result can be stored and displayed.

This process can be repeated for each low-energy AMRT in the digestion mixture. Further analysis can be performed on the results including storing the results, displaying the results, quantitation and combining the results with those of other injections.

During the search, multiple charge states and multiple isotopes can be searched. In addition, the ions, or the charged reduced AMRTs could be searched. Further, empirically produced confidence rules can be applied to help identify valid hits, and better confidence is obtained with a higher number of high-energy hits.

In summary, given a set of data acquired by an LC/MS system, known protein identification techniques search a database of theoretical protein sequences to identify the proteins in the data. That is, known protein identification techniques start with the data and search a database. The invention described below, in contrast, starts with the database and searches the data.

BRIEF SUMMARY OF THE INVENTION

In contrast to conventional protein identification techniques, embodiments of the present invention, start with a theoretical peptide sequence (generally, but not always, obtained from a protein database), and search the data for evidence of precursor and fragment ions that correspond to the theoretical peptide sequence. If a sufficient number of such masses are found in the data, and at a common retention time, then the peptide sequence is identified in the data. If this method finds in the data one or more peptide sequences associated with a given protein, then the protein is taken to be identified in the sample.

Embodiments of the present invention search the data obtained using an LC/MS system using a preselected database. For example, in one embodiment of the present invention, an eluent output by the liquid chromatograph (LC) is introduced into a mass spectrometer (MS) through an ESI interface. The first quadrupole (Q1) of the MS functions simply as an ion guide. An alternating voltage is applied to a collision cell. Spectra are collected of all precursors and all of their fragments in an alternating fashion as described in Bateman.

More specifically, embodiments of the present invention collect spectra that alternate uniformly in time between a low-energy mode and a high-energy mode. There is no MS spectral selection applied prior to high-energy fragmentation. The high-energy mode spectra contain fragment ions of all precursor ions. Because of the high-duty cycle of the alternating mode of data acquisition, the chromatographic profiles of all detected precursors and fragments are preserved. This mode of data acquisition enables determination or measurement of the retention times, as well as m/z and intensities of all ions seen in the low and in the high-energy modes.

The low-energy mode corresponds to conventional LC/MS acquisition. The high-energy mode is alternatively referred to herein as elevated-energy mode. The high-energy or elevated-energy mode corresponds to LC/MS$^E$ acquisition. The low-energy mode contains spectra of primarily precursor ions. The high-energy mode contains spectra of primarily fragment ions.

BRIEF DESCRIPTION OF THE DRAWINGS

FIG. 4C shows an example of a precursor peptide sequence in the database that appears to have a significant number of hits at approximately 78 minutes.

FIG. 5C shows an example of a precursor peptide sequence in the database that appears to have a significant number of hits at approximately 78 minutes.

DETAILED DESCRIPTION OF THE INVENTION

Glossary

Figure 1:
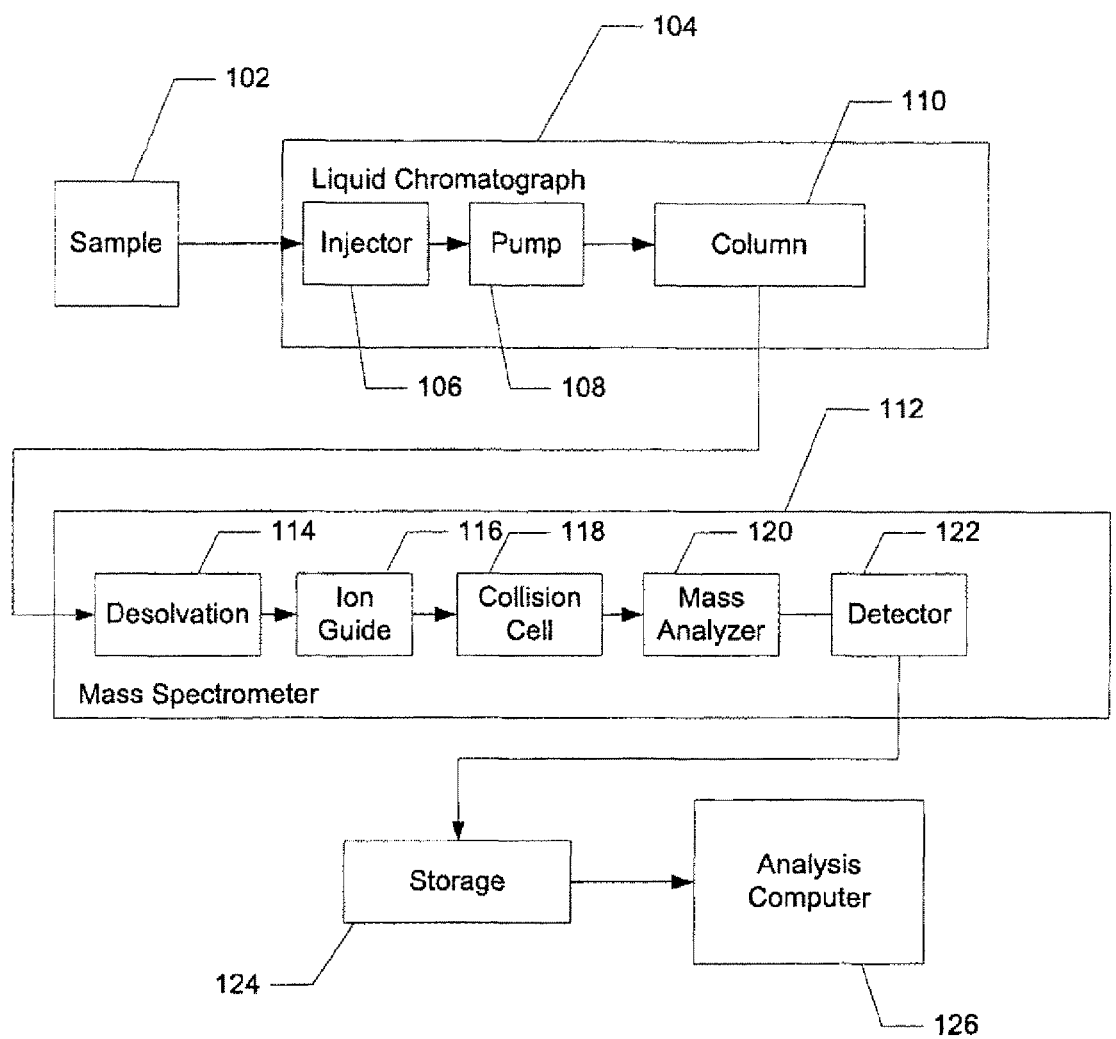
FIG. 1 is a schematic diagram of a system for identifying and quantifying proteins in a complex biological mixture according to an embodiment of the present invention.

As used herein, the following terms have the specified meanings:

Protein—a specific primary sequence of amino acids assembled as a single polypeptide.

Peptide—a specific sequence of amino acids assembled as a single polypeptide contained within the primary sequence of a protein.

Tryptic peptides—peptides generated from a protein sequence that result from enzymatic cleavage of the protein by trypsin. In the ensuing description, digest peptides are referred to as tryptic peptides for convenience. However, it should be understood that embodiments of the present invention apply to other techniques for peptide digestion.

Precursor peptides—tryptic peptides (or other protein cleavage products) that are directly generated using the protein cleavage protocol. The precursor peptides from the sample are separated chromatographically and passed to mass spectrometer. In the mass spectrometer, the ion source ionizes these precursor peptides to produce a positively charged, protenated form of the precursor. The mass of such positively charged protenated form can be referred as the mwHPlus or MH+ of the precursor. In the following, we use the term "precursor mass" refers generally to the protenated, mwHPlus or MH+ mass of the ionized, peptide precursor.

Fragments—Multiple types of fragments can occur in $MS^E$ spectra. In the case of tryptic peptide precursors, fragments can include polypeptide ions that are produced from collisional fragmentation of the intact peptide precursors and whose primary amino acid sequence is contained within the originating precursor peptide. Y-ions and B-ions are examples of such peptide fragments. Fragments of tryptic peptides can also include immonium ions, functional groups such as a phosphate ion ($PO_3$), mass tags cleaved from a specific molecule or class of molecules, or "neutral loss" of water ($H_2O$) or ammonia ($NH_3$) molecules from the precursor.

Y-ions and B-ions—If a peptide fragments at the peptide bond, then if a charge is retained on the N terminal fragment, that fragment ion is termed a B-ion. If the charge is retained on the C terminal fragment, the fragment ion is termed a Y-ion. A more comprehensive list of possible fragments and their nomenclature is provided in See Roepstorff and Fohlman, Biomed Mass Spectrom, 1984; 11(11):601, and Johnson et al, Anal. Chem. 1987, 59(21): 2621:2625, both of which are hereby incorporated by reference.

Chromatographic profile—the intensity versus time of a chromatographic peak at a single mass corresponding to a single precursor or fragment ion in an LC/MS analysis. Mass chromatograms can contain chromatographic profiles of one or more such ions.

Apex retention time or chromatographic retention time—the point in a chromatographic profile at which an entity reaches its maximum intensity during an LC/MS analysis.

Ions—each peptide appears as an ensemble of ions due to the natural abundance of the isotopes of the constituent elements. An ion has a retention time and an m/z value. The mass spectrometer (MS) detects only ions. The LC/MS technique produces a variety of observed measurements for every detected ion. This includes: the charge-to-mass ratio (m/z) m, the retention time, and the signal intensity of the ion.

MwHPlus—The neutral, monoisotopic mass of the peptide plus the weight of one proton, 1.007825 amu.

AMRT—accurate mass retention time. The AMRT is an empirical description of a peptide in terms of its mass, retention time and total intensity. When a peptide elutes from the chromatographic column, it elutes over a specific retention time period and reaches its maximum signal at a single retention time (apex retention time). After ionization and (possible) fragmentation, the peptide appears as a related set of ions. The different ions in the set correspond to different isotopic compositions and charges of the common peptide. Each ion within the related set of ions produces a single apex retention time and peak shape. Since these ions originate from a common peptide, the apex retention time and peak shape of each ion is identical, within some measurement tolerance. The MS acquisition of each peptide produces multiple ion detections for all isotopes and charge states, all sharing the same identical apex retention-time and peak shape within some measurement tolerance.

In an LC/MS separation, a single peptide (precursor or fragment) produces many ion detections, which appears as a cluster of ions, at multiple charge states. Deconvolution of these ion detections from such a cluster, indicates the presence of a single entity of a unique monoisotopic mass, at a specific retention time, of a measured signal intensity, in a charge state, giving rise to the AMRT.

It is not possible to infer directly from an AMRT whether it is a precursor, or a fragment, or a chemically modified peptide, let alone what its sequence is. Molecules other than peptides can be described using AMRTs.

Protein Database—In embodiments of the present invention, the user selects or otherwise supplies a database of proteins. Alternatively, a default database or other predetermined database can be used. Each protein is described by its primary sequence of amino acids. It is up to the user to choose which database (or database subset) is to be compared to the data. A user might choose a database that is intended to closely match the proteins under study. For example, an E. Coli database would be compared to data obtained from a cell lycate of E. Coli. Similarly, a human serum database would be compared to data obtained from human serum. A user could choose a subset database. A user could choose a superset database, such as all proteins listed in SwissProt. A user could choose a data a base that contains simulated proteins, described by random sequences of amino acids. Such random databases are used in control studies to evaluate or calibrate protein identification systems and search algorithms. A user could choose a database that combines both naturally occurring and artificial sequences.

From the protein database, software can infer from each sequence, the sequence and masses of tryptic precursor ions, Y- and B-ions, and other possible fragment ions that would result from those precursors.

DETAILED DESCRIPTION

FIG. 1 is a schematic diagram of a system for identifying and quantifying proteins in a complex biological mixture according to an embodiment of the present invention. A sample 102 is injected into a liquid chromatograph 104 through an injector 106. A pump 108 pumps the sample through a column 110 to separate the mixture into component parts according to retention time through the column.

The output from the column is input to a mass spectrometer 112 for analysis. Initially, the sample is desolvated and ionized by a desolvation/ionization device 114. Desolvation can be any technique for desolvation, including, for example, a heater, a gas, a heater in combination with a gas or other desolvation technique. Ionization can be by any ionization techniques, including for example, electrospray ionization (ESI), atmospheric pressure chemical ionization (APCI), matrix assisted laser desorption (MALDI) or other ionization technique. Ions resulting from the ionization are fed to a collision cell 118 by a voltage gradient being applied to an ion guide 116. Collision cell 118 can be used to pass the ions (low-energy) or to fragment the ions (high-energy). For example, as described in Bateman, an alternating voltage can be applied across the collision cell 118 to cause fragmentation. Spectra are collected for the precursors at low-energy (no collisions) and fragments at high-energy (results of collisions).

The output of collision cell 118 is input to a mass analyzer 120. Mass analyzer 120 can be any mass analyzer, including quadrupole, time-of-flight (TOF), ion trap, magnetic sector mass analyzers as well as combinations thereof. A detector 122 detects ions emanating from mass analyzer 122. Detector 122 can be integral with mass analyzer 120. For example, in the case of a TOF mass analyzer, detector 122 can be a microchannel plate detector that counts intensity of ions, i.e., counts numbers of ions impinging it.

A storage medium 124 provides permanent storage for storing the ion counts for analysis. For example, storage medium 124 can be an internal or external computer disk. An analysis computer 126 analyzes the stored data. Data can also be analyzed in real time without requiring storage in a storage medium 124. In real time analysis, detector 122 passes data to be analyzed directly to computer 126 without first storing it to permanent storage.

Collision cell 118 performs fragmentation of the precursor ions. Fragmentation can be used to determine the primary sequence of a peptide and subsequently lead to the identity of the originating protein.

Collision cell 118 includes a gas such as helium, argon, nitrogen, air, or methane. When a charged peptide interacts with gas atoms, the resulting collisions can fragment the peptide by breaking it up at one or more characteristic bonds. The most common resulting fragments are described as Y- or B-ions. Such fragmentation can be accomplished as on-line fragmentation by switching the voltage in a collision cell between a low voltage state (low energy, <5 V) which obtains MS spectra of the peptide precursor, with a high voltage state (high energy, >15V) which obtains MS spectra of the collisionally induced fragments of the precursors. High and low voltage are referred to as high and low energy, since a high or low voltage respectively is used to impart kinetic energy to an ion.

Various protocols can be used to determine when and how to switch the voltage for such an MS/MS acquisition. For example, conventional methods trigger the voltage in either a targeted or data dependent mode (data-dependent analysis, DDA). These methods also include a coupled, gas-phase isolation (or pre-selection) of the targeted precursor. The low-energy spectra are obtained and examined by the software in real-time. When a desired mass reaches a specified intensity value in the low-energy spectrum, the voltage in the collision cell is switched to the high-energy state. The high-energy spectra are then obtained for the pre-selected precursor ion. These spectra contain fragments of the precursor peptide seen at low energy. After sufficient high-energy spectra are collected, the data acquisition reverts to low-energy in a continued search for precursor masses of suitable intensities for high-energy collisional analysis.

Although conventional switching techniques can be employed, embodiments of the present invention preferably use a novel fragmentation protocol in which the voltage is switched in a simple alternating cycle. This switching is done at a high enough frequency so that multiple high- and multiple low-energy spectra are contained within a single chromatographic peak. Unlike conventional switching protocols, the cycle is independent of the content of the data.

In summary, each sample 102 is injected into the LC/MS system. The LC/MS system produces two sets of spectra, a set of low-energy spectra and a set of high-energy spectra. The set of low-energy spectra contain primarily ions associated with precursors. The set of high-energy spectra contain primarily ions associated with fragments. These spectra are stored in a storage medium 124. After data acquisition, these spectra can be extracted from the storage medium and displayed and processed by post-acquisition algorithms in the analysis computer 126.

The data acquired by the high-low protocol allows for the accurate determination of the retention times, mass-to-charge ratios, and intensities of all ions and AMRTs collected in both low- and high-energy modes. In general, different ions are seen in the two different modes, and the spectra acquired in each mode are then analyzed separately to determine the retention times, mass-to-charge ratios and intensities of the ions seen in the respective mode.

Figure 2:
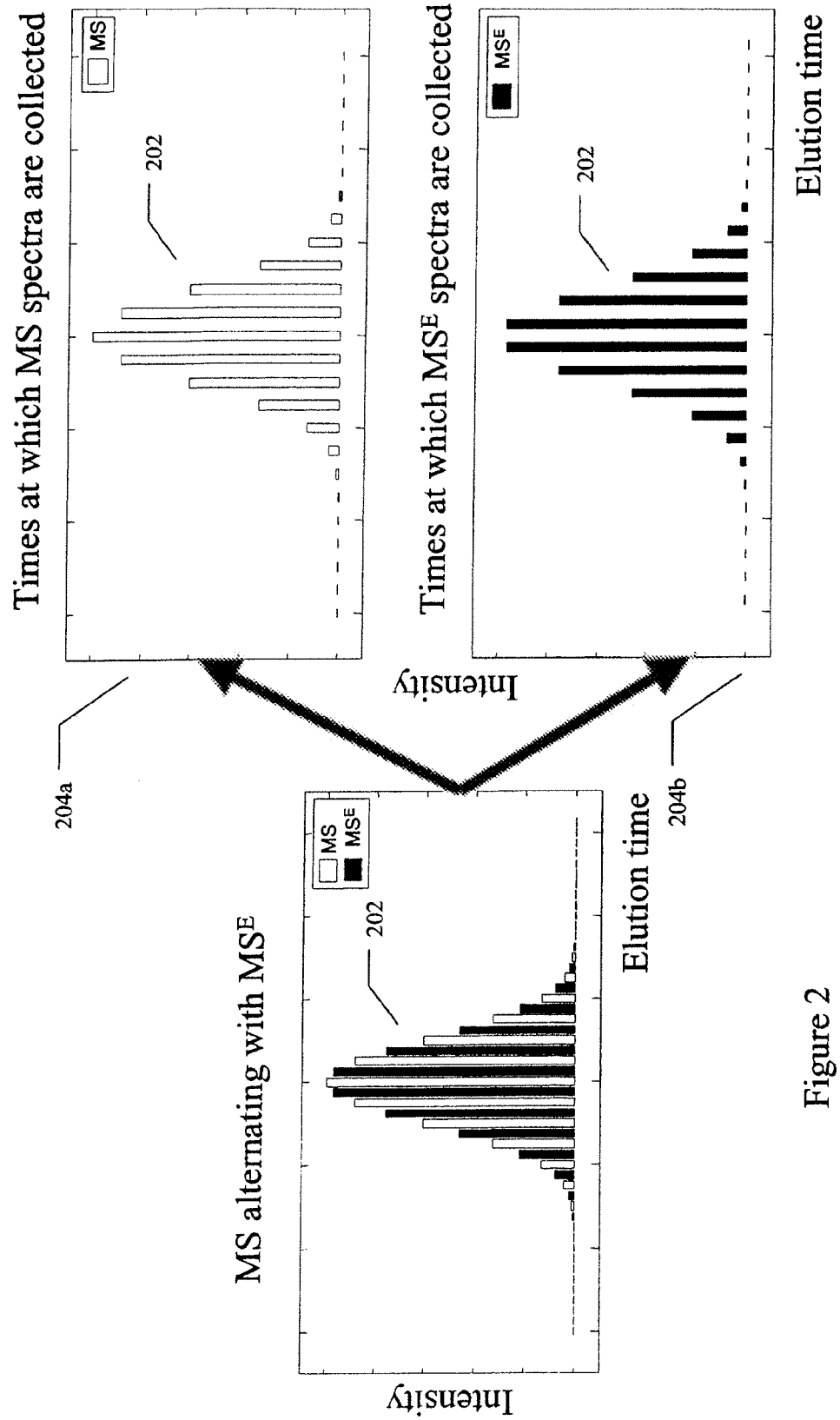
FIG. 2 illustrates times at which exemplary spectra are acquired. These spectra result from application of the alternating low- and high-energy modes according to an embodiment of the present invention.

The ions from a common precursor as seen in one or both modes will share the same retention times and peak shapes. The high-low protocol allows the meaningful comparison of retention time and peak shape of ions within a mode and between modes. This comparison can then be used to group ions seen in both low-energy and high-energy spectra by their common retention time and peak shape. FIGS. 2, 8, and 9 and the following discussion show how the low-energy spectra and the high-energy spectra can be used to find ions that have common retention times and peak shapes.

FIG. 2 illustrates the times at which spectra are obtained during the elution of a peak resulting from application of the alternating low- and high-energy modes according to an embodiment of the present invention. FIG. 2 shows that the chromatographic profiles and retention time of ions associated with the precursors can be reconstructed for both the high- and low-energy spectral data.

Peak 202 represents the chromatographic elution profile of a single precursor. The horizontal axis is elution time. The vertical axis is arbitrary, and represents the time-varying concentration, the chromatographic profile, of the precursor as it elutes from the chromatographic column.

Plots 204a (low-energy) and 204b (high-energy) in FIG. 2 depict the same chromatographic peak 202, wherein the horizontal axis represents time and the vertical axis represents intensity of an ion.

An eluting molecule, passed to the mass spectrometer, produces ions in both low- and high-energy modes. The ions produced in the low-energy mode are primarily those of the precursor ions in possibly different isotopic and charge states. In proteomic studies, the precursor ions are peptides generated from enzymatic digestion (typically a tryptic digest) of the intact protein(s). In high-energy mode, the ions are primarily different isotopes and charge states of the fragment ions of those precursors. High-energy mode can also be referred to as elevated-energy mode.

In the plot of peak 202, the alternating bars of different density represent the times at which spectra were collected with low and high-energy voltages during the elution of the depicted chromatographic peak. The bars alternate uniformly in time. Plot 204a illustrates exemplary the times at which low-energy voltage was applied in the collision cell, resulting in low-energy spectra. Plot 204b illustrates times at which high-energy voltage was applied in the collision cell, resulting in high-energy spectra. As shown in FIGS. 204a and 204b, the chromatographic peak is sampled multiple times, by the high- and low-energy modes. From these multiple samples, accurate retention times of all the ions associated with the peak and seen in the high- and low-energy spectra can be inferred. These accurate retention times are obtained by interpolation of the intensities sampled by the respective spectra.

Figure 8A:
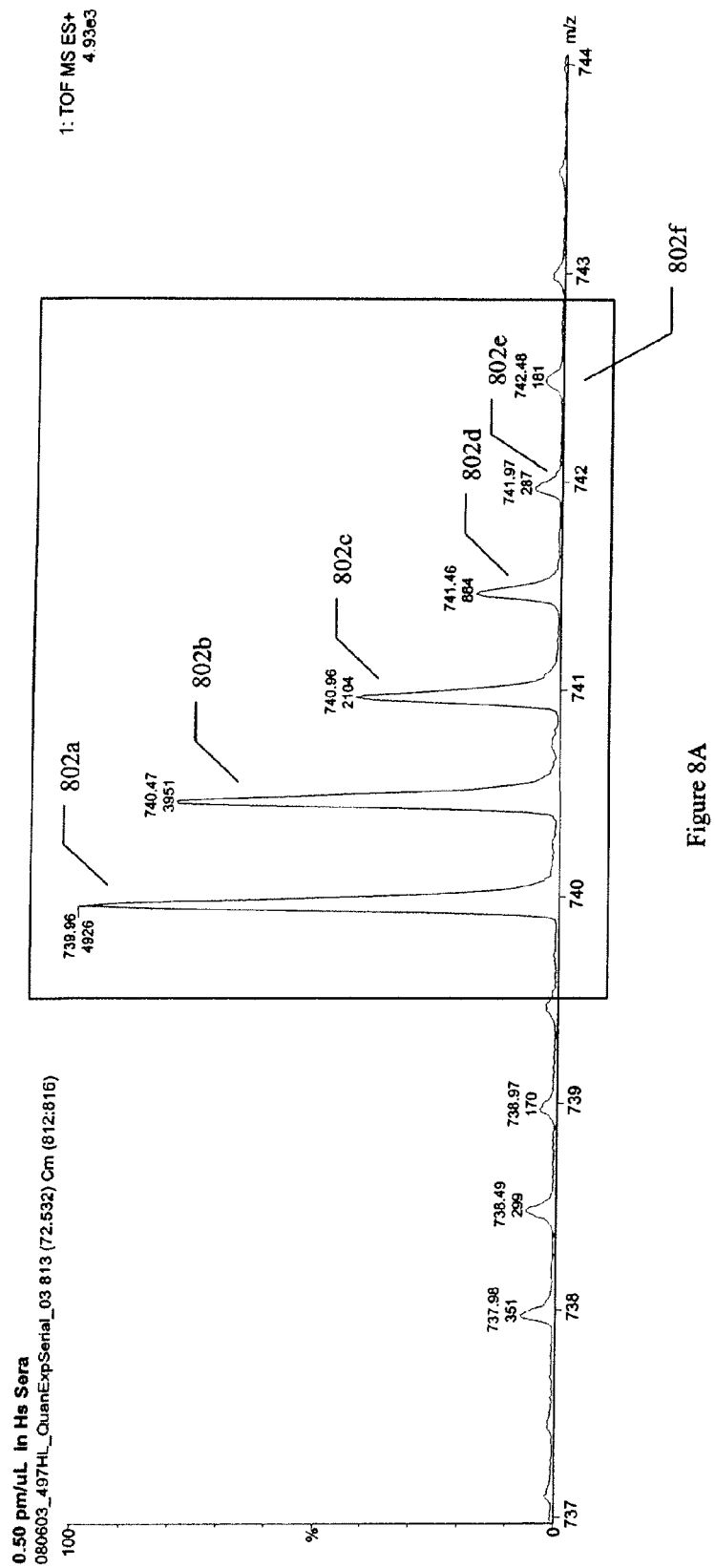
FIG. 8A illustrates an exemplary spectrum of a peptide.
Figure 8B:
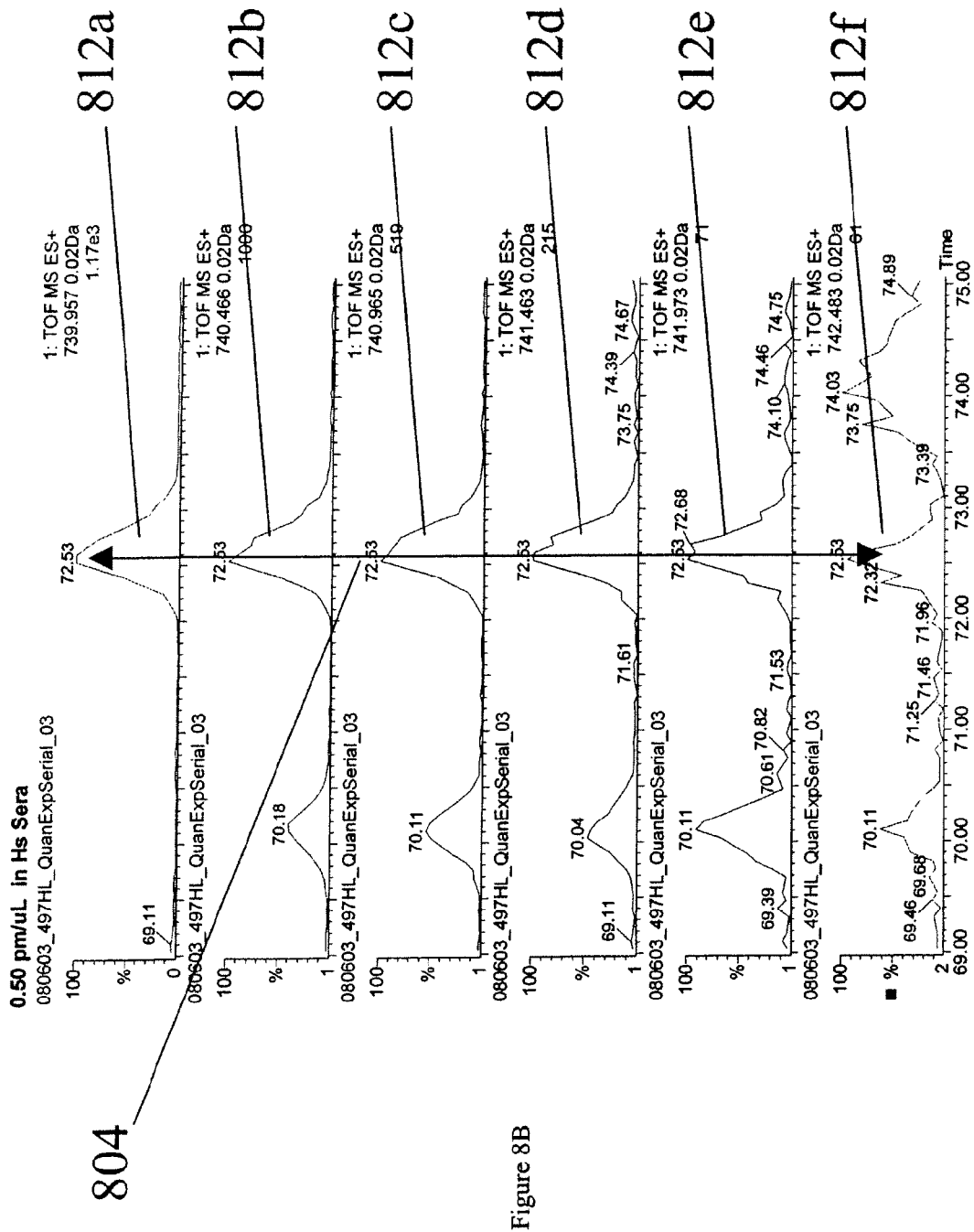
FIG. 8B illustrates a series of mass chromatograms corresponding to each of the six ions illustrated in FIG. 8A.

For a molecule that elutes at a retention time, $t_r$, all associated ions will also be seen to elute at exactly the same retention time to within some measurement precision. This phenomenon is demonstrated in FIGS. 8A-B and 9A-C. Ions associated with a common precursor have identical chromatographic peak shapes. FIGS. 8A-B illustrate an exemplary spectrum extracted at 72.5 minutes that contains isotopes of a Z=+2 ion. The six ions 802a-f (appearing in mass 740-742.5 amu) shown in FIGS. 8A-B are isotopes from a tryptic peptide of the serotransferrin precursor protein in human serum. The peptide's sequence is MYLGYEYVTAIR. The spacing between the mass-to-charge (m/z) of the ions is 0.5 amu, indicating that the charge of the ion is Z=2. At Z=2, the m/z value for the $^{12}C$ monoisotopic ion is 739.96 amu.

FIG. 8B illustrates a series of mass chromatograms corresponding to each of the six ions illustrated in FIG. 8A. As indicated by a vertical line 804, the retention time of each ion has the same value of 72.53 min, indicating that the chromatographic apex of each ion falls within the same, single scan. Vertical line 804, with arrow heads, indicates that the retention times of each of the six chromatographic peaks, 812a-f, is the same, confirming that the ions seen in the top plot are related to a common precursor.

Figure 9A:
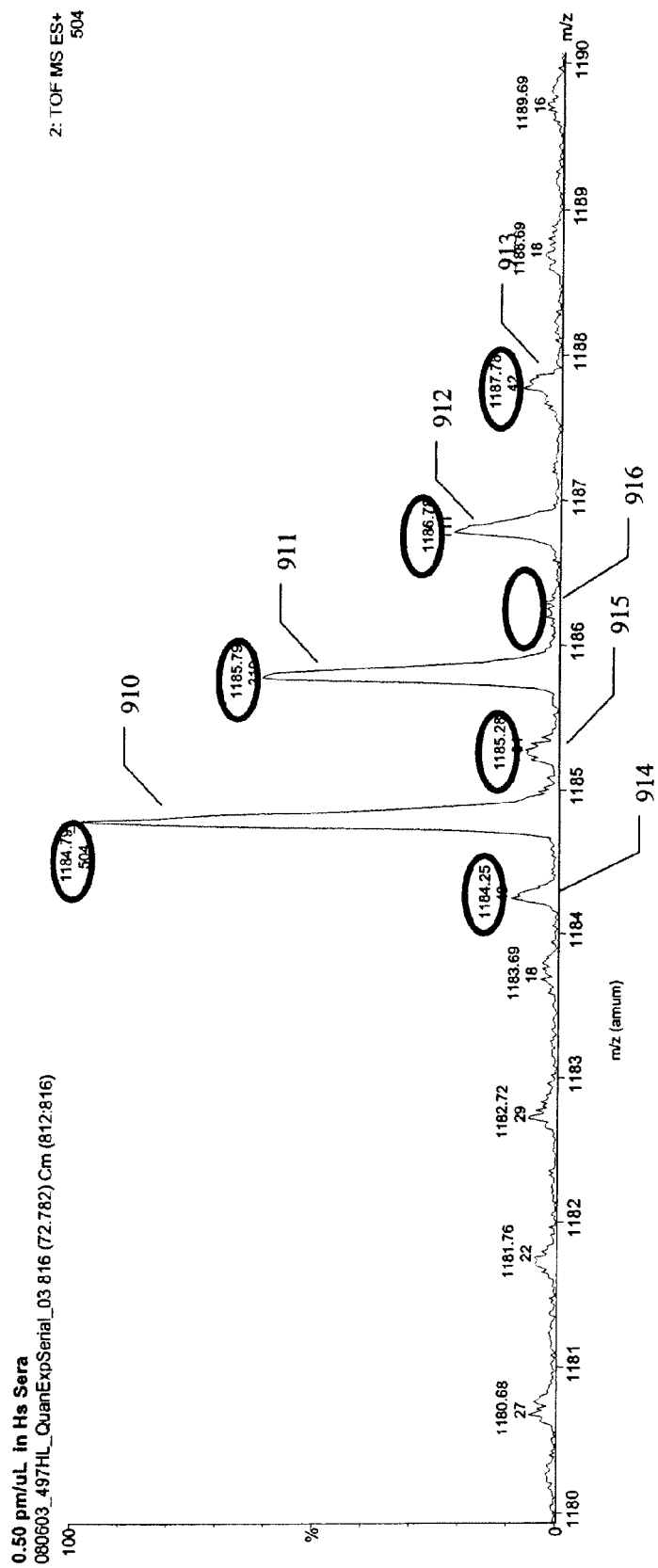
FIG. 9A is a plot of an exemplary high-energy spectrum showing many spectral peaks.

FIG. 9A is a plot of an exemplary high-energy spectrum showing many spectral peaks 910-916. FIG. 9C is a series of plots illustrating the chromatographic profile corresponding to several of the peaks that appear in FIG. 9A. Spectral peaks 910,911,912, and 913 have corresponding chromatographic peaks plotted in FIG. 9C as peaks 920, 921, 922, and 923. The chromatographic peaks of these four spectral peaks have substantially the same peak shape and retention time, consistent with the hypothesis that they are from the same peptide. Spectral peaks 914, 915, and 916, correspond to chromatographic peaks 924, 925, and 926. The retention times of peaks 924, 925, and 926 are substantially the same, as are their peak shapes, consistent with the hypothesis that that spectral peaks 914, 915, and 916 are from the same peptide.

Figure 9B:
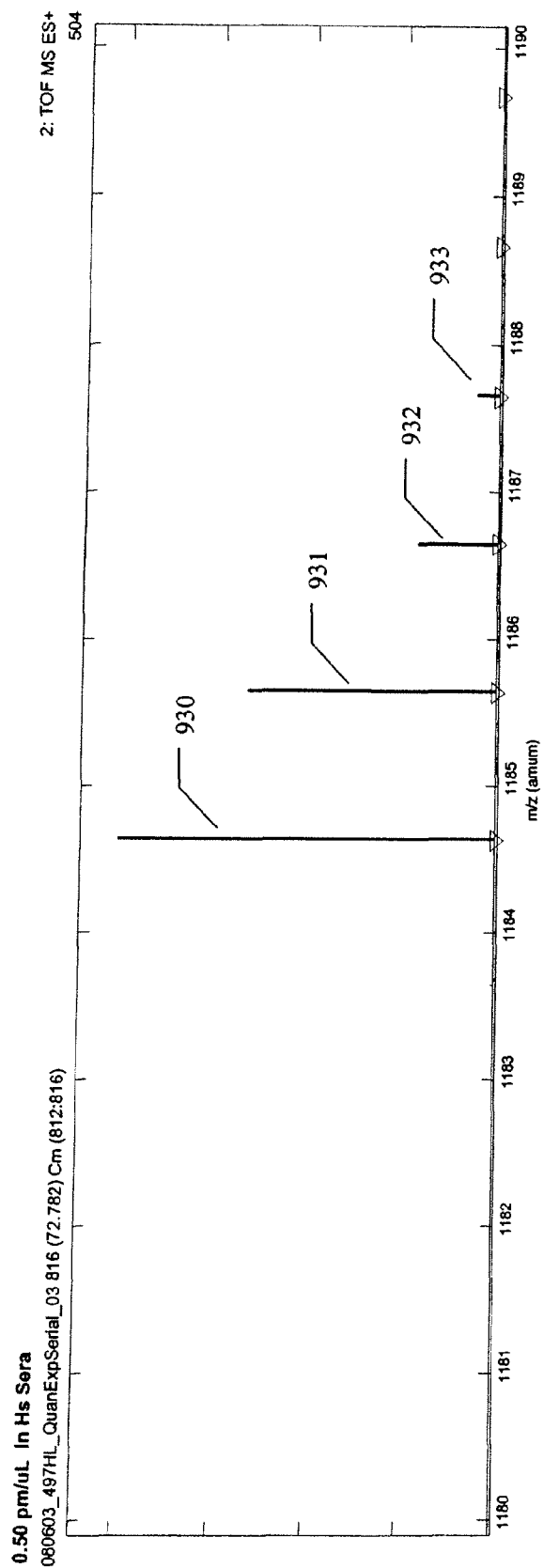
FIG. 9B plots only those spectral peaks that have identical retention time to that of one of the peaks illustrated in FIG. 9A.
Figure 9C:
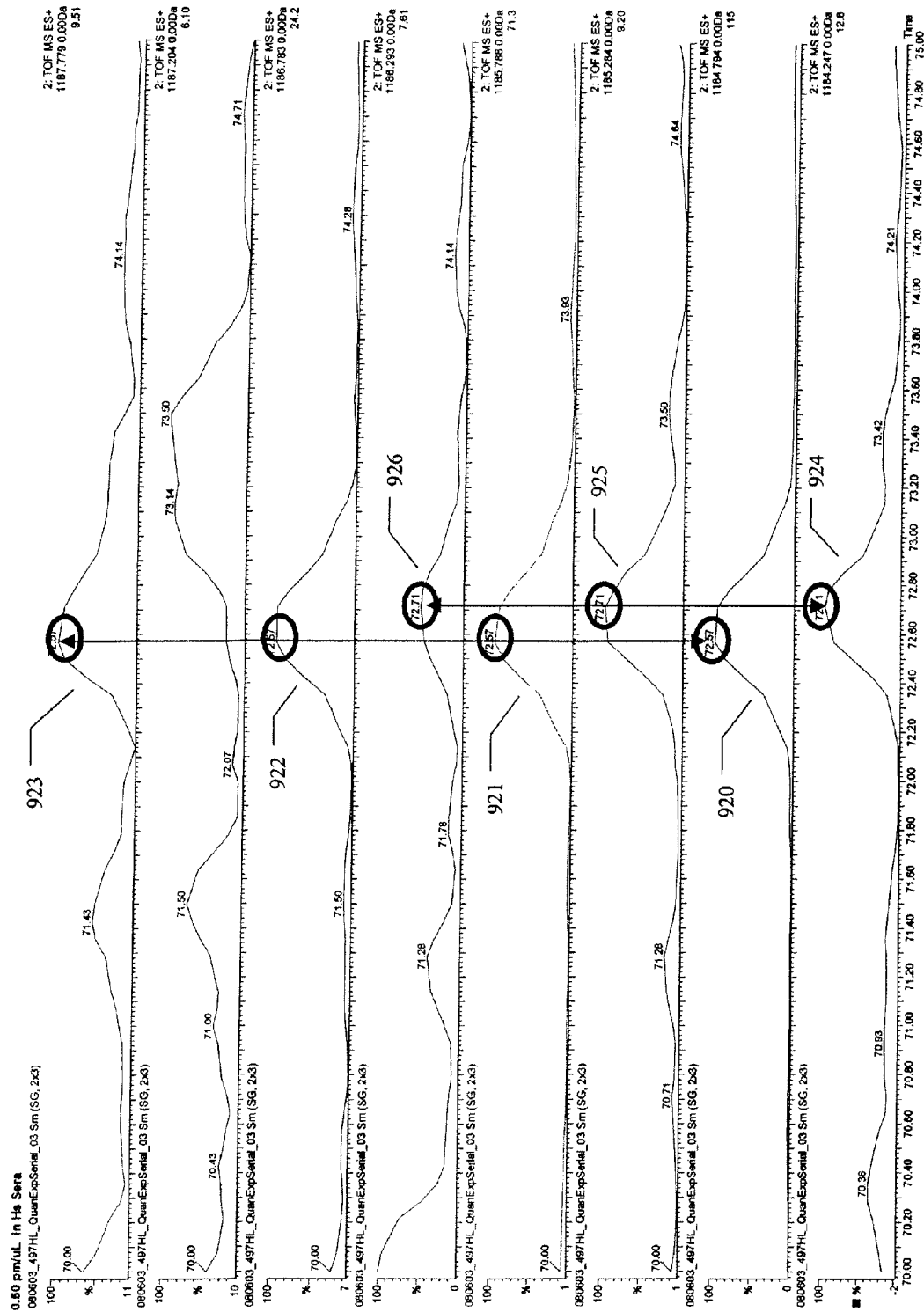
FIG. 9C is a series of plots illustrating the chromatographic profile corresponding to most of the peaks that appear in FIG. 9A.

FIG. 9B plots only those spectral peaks that have identical retention time to that of peak 910. Thus only peaks 910, 911, 912, and 913, are re-plotted as vertical lines 930, 931, 932, 933 in FIG. 9B. All other peaks in FIG. 9A are excluded and not plotted in FIG. 9B because of retention time match misalignment. This example demonstrates that chromatographic information can be used to select related spectral peaks, or exclude unrelated peaks. As described below, the PDS algorithm of embodiments of the present invention relies on correspondence in retention time between a precursor and its fragments, as seen in both low- and high-energy spectra.

Figure 3A:
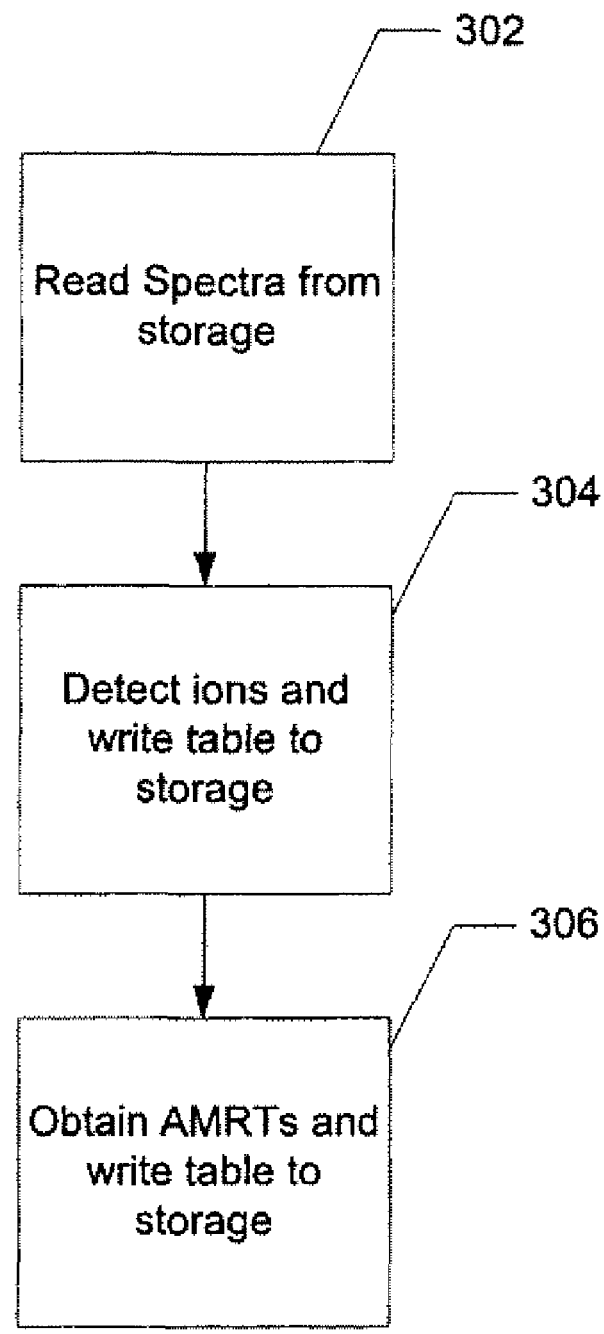
FIGS. 3A-3C are flow charts for a method for peptide identification according to an embodiment of the present invention.
Figure 3B:
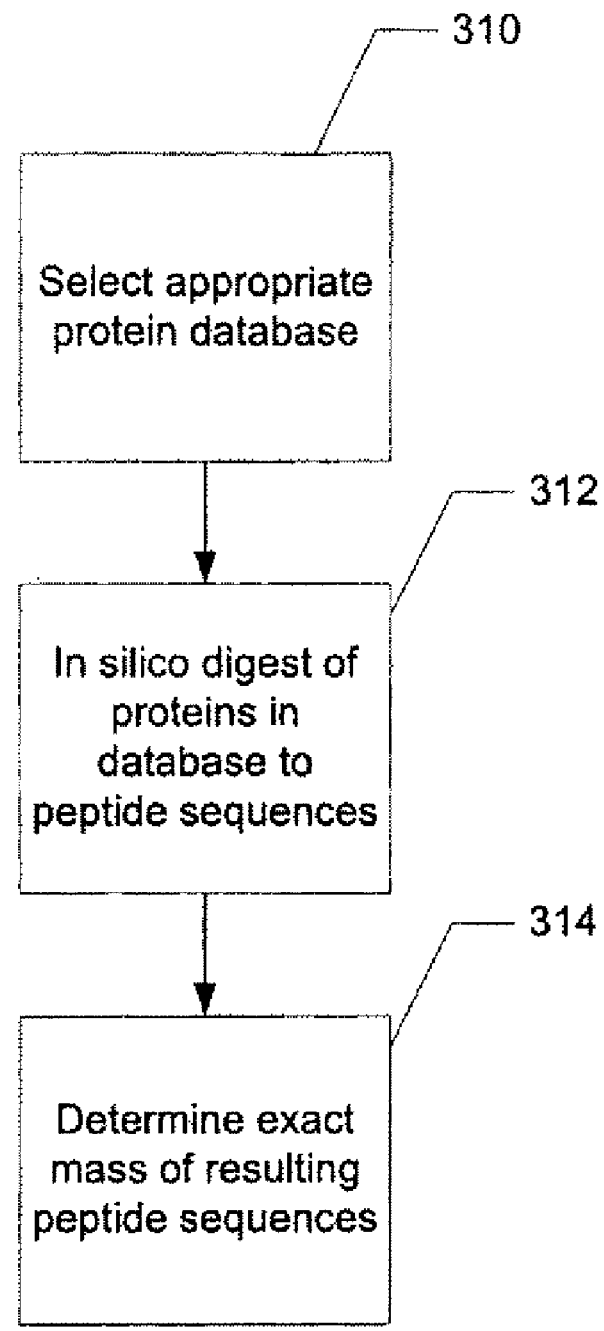
Figure 3C:
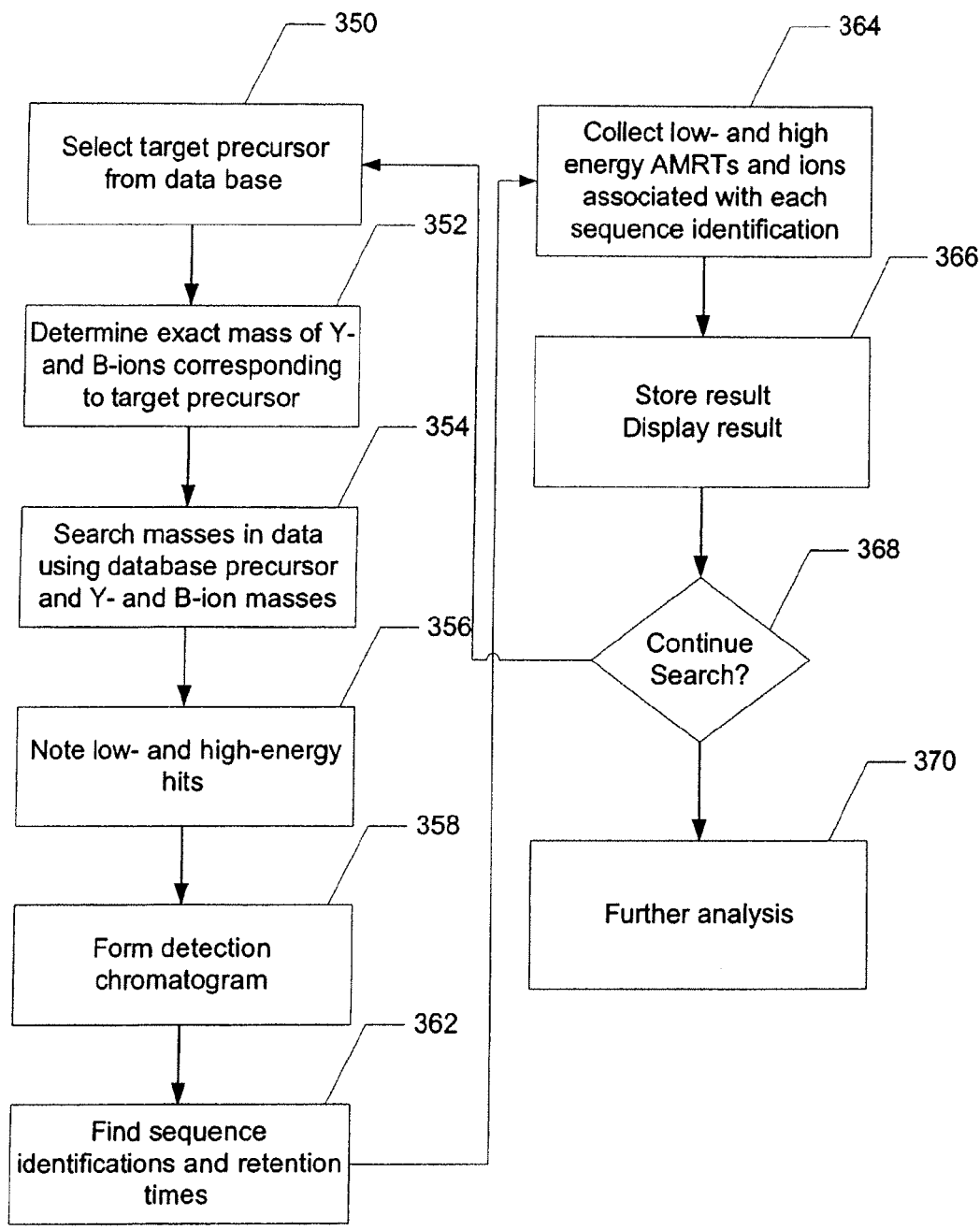

FIGS. 3A-C are flowcharts for a method for peptide identification according to an embodiment of the present invention. For ease of reference, the method of the present invention is called the peptide data search (PDS) algorithm. Given a peptide sequence corresponding to a protein in an exact mass database, embodiments of the present invention search the data to determine if the peptide sequence is present. Prior knowledge about the peptide's retention time is not required. However, knowing a range of times at which the peptide elutes can help reduce the number of data AMRTs searched. This reduction speeds up the computation and reduces the rate of false positive detections. It also allows a lower detection threshold (described below) to be applied to the detection chromatogram.

Prior to searching the data, ions or AMRTs must be obtained from both the low- and high-energy data. FIG. 3A is a flowchart for a method for obtaining the ions or AMRTs according to an embodiment of the present invention. The method of FIG. 3A is applied to both the low- and high-energy data to obtain the required ions or AMRTs.

In step 302, collected spectra are read from the hard drive. In step 304, ions are detected from the spectra. For example, ions can be detected by peak finding algorithms applied to spectra and mass chromatograms as described by Bateman (U.S. Pat. No. 6,717,130), or by two-dimensional convolution techniques described in co-pending PCT Application No. PCT/US05/04180, filed Feb. 11, 2005, entitled "Apparatus and Method for Identifying Peaks in Liquid Chromatography/Mass Spectrometry Data and for Forming Spectra and Chromatograms," (the "'4180 Application"), hereby incorporated by reference. In an embodiment of the present invention, the measured properties of an ion are its retention time, mass-to-charge ratio (m/z), and intensity. Step 304 stores a list of these ion properties in a table. From this table, the list of these ions and their properties is input to method 306. Method 306 determines accurate mass retention times (AMRTs) and writes AMRT parameters into a table and stores these parameters.

In an LC/MS experiment, a peptide appears as a set of ions, each ion corresponds to a peptide in a different isotopic and charge state. An AMRT is the set of ions generated by a peptide. The properties of an ARMT are determined from the set of ions that comprise an AMRT.

An AMRT corresponds to a set of ions from the ion list obtained in step 304. Thus method 306 parses the ion list into sets of ions, where each set is an AMRT. The properties of an ARMT are determined from such sets. An AMRT is described by four parameters: a retention time, mwHPlus, intensity, and fractional charge state. An AMRT consists of a set of at least 2 or more ions. Two or more ions are needed to establish the charge and, hence, the mwHPlus of an ARMT.

The retention time and mwHPlus of an AMRT is the retention time and mwHPlus of the lowest mass, monoisotopic ion in the set. The intensity of the AMRT is the sum of the intensities of the ions in the set. It is also possible to derive for each AMRT a figure of merit known as a fractional charge state. The fractional charge state is the sum of the charges of each ion, weighted by fractional intensity of that ion with respect to the AMRT intensity. Ions not assembled into a set are treated as single ions, described by their retention time, m/z and intensity. A single ion can be effectively considered to be an AMRT if a charge for that ion is assumed or assigned by a rule.

The mwHPlus of a peptide is the neutral, monoisotopic mass of the peptide plus the mass of one proton, referred to as [M+H], or mwHPlus, or MH$^+$. The monoisotopic mass M is the mass of the peptide when all its atoms are in their lowest mass, most abundant isotopic state.

The PDS and EDA algorithms (described below) as applied to peptides take as input an AMRT's retention time, mwHPlus, and intensity. The list of single ions is stored with the AMRT list. A single ion can be effectively considered to be an AMRT if a charge for that ion is assumed or assigned by a rule. Thus single ions can be optionally included with the ARMT list as input to the PDS and EDA algorithms. Alternatively, the PDS and EDA algorithms (as described below) can be applied only to the ions, as obtained in step 304, bypassing step 306.

The algorithm implemented in step 306 makes use of known properties of the mass spectrometric properties of peptides. It is known that a peptide appears in a mass spectrum as a set of ions at different values of m/z. Examples of such spectra are described in *Mass Spectrometry of Biological Materials*, by Barbara Seliger Larsen (Editor), Charles N. McEwen (Editor), Marcel Dekker; 2nd Rev edition (Mar. 1, 1998), pages 34-46, hereby incorporated by reference.

A peptide ion can have possible mass-to-charge ratios of $$m/z=[M+Z\times H+N\times 1.003]/Z=[M+N\times 1.00335]/Z+H.$$

where M is the monoisotopic mass of the neutral peptide, H=1.00728 amu, is the mass of the proton responsible for the peptide's charge, Z is the peptide's charge, N is isotope number of the peptide (an integer), and 1.00335 amu is the mass difference between $^{13}C$ and $^{12}C$ isotopes. This mass difference is an approximation to the actual mass differences that occur between isotopes of the same peptide.

The value for N=0 corresponds to this monoisotopic state. The monoisotopic mass of the peptide for N=0 and for Z=1 is then [M+H].

FIG. 8A shows a portion of a mass spectrum that contains a set of 6 ions 802a-f associated with a single peptide. Such a set is commonly referred to as a cluster, or ion cluster. The spacing in m/z between the ions in this cluster is 0.5 amu, evidence that the ions are different isotopic states of a peptide having charge Z=2. The lowest mass ion is the monoisotope and appears at m/z=739.96. We infer the mwHPlus of the peptide to be 739.96*2−1.00739=1478.91 amu. If this peptide appears at charge Z=1, then the monoisotope will appear at m/z of 1478.91 amu, and if the peptide appears at Z=3, the monoisotope will appear at (1478.91+2)/3=493.64 amu. The mass spectrum of a peptide can be described as consisting of one or more clusters of ions; each cluster corresponds to ions of the same charge; and the different clusters correspond to the ions in different charge states.

In the LC/MS data generated here, an AMRT appears as a set of ions where each ion is described by a retention time, m/z, and intensity. It is straightforward to infer, from the ion list obtained in step 304, sets of ions, where each set corresponds to an AMRT, and each such AMRT is inferred to correspond to a peptide. Because we assume each AMRT derives from a peptide, we can make use of rules to arrive at such sets. For example, ions from a peptide must occur at a common retention time (as described by Bateman), and the mass-to-charge relationships between ions in such a set must conform to the rules described above. The method 306 then collects sets of ions whose properties satisfy such rules. Each such set corresponds to an AMRT, and each such AMRT is inferred to correspond to a peptide.

The method in 306 is then applied to the ion list obtained from the low-energy spectra to obtain the low-energy AMRTs. It is also applied independently to the high-energy ion list obtained from the high-energy spectra to obtain the high-energy AMRTs.

In summary, step 306 determines an AMRT to be a set of ions where each ion in the set is inferred to arise from a single, common peptide. The peptide can be a precursor or fragment. Step 306 makes use of the known properties of peptide spectra as described and illustrated above, and the common retention time of such ions, to infer the sets of ions that correspond to AMRTs. Step 306 then computes the AMRT parameters (retention time, mwHPlus, intensity, and fractional charge state) from each ion set and stores those parameters and notes the ions comprising each set.

Known algorithms deconvolve ions seen peptide spectra in order to infer their charge state Z and mwHPlus. An example of such algorithms is given in *Role of Accurate Mass Measurement (+/−10 ppm) in Protein Identification Strategies Employing MS or MS/MS and Database Searching* Karl R. Clauser, Peter Baker, and Alma L. Burlingame, Anal. Chem. 1999, 71, 2871-2882. Another such algorithm is *A Universal Algorithm for Fast and Automated Charge State Deconvolution of Electrospray Mass-to-Charge Ratio Spectra*, Zhongqi Zhang and Alan G. Marshall, J. Am. Soc. Mass Spectrom. 1998, 9, 224-233, each of which is hereby incorporated by reference.

But these known algorithms operate only on single spectra. Thus such algorithms can determine the charge state and mwHPlus of each peptide seen in a spectrum, but cannot determine an accurate retention time for such peptides.

Figure 17A:
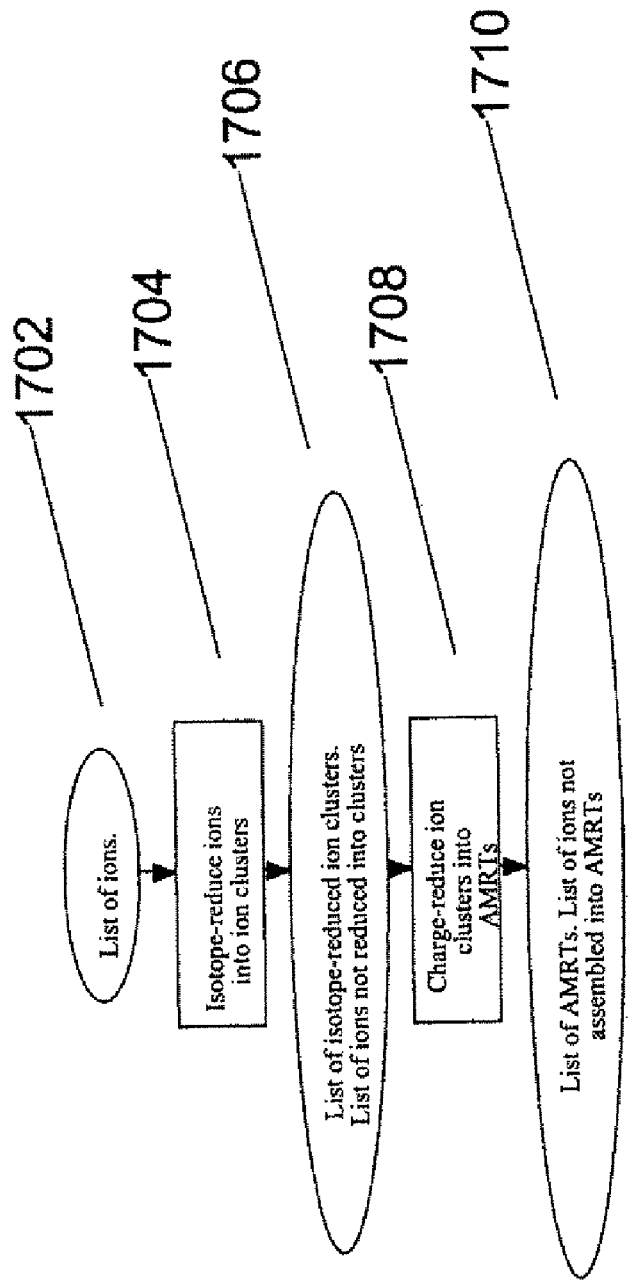
FIGS. 17A-17C contain flow charts for a method for the determination of AMRTs from an ion list according to an embodiment of the present invention.
Figure 17B:
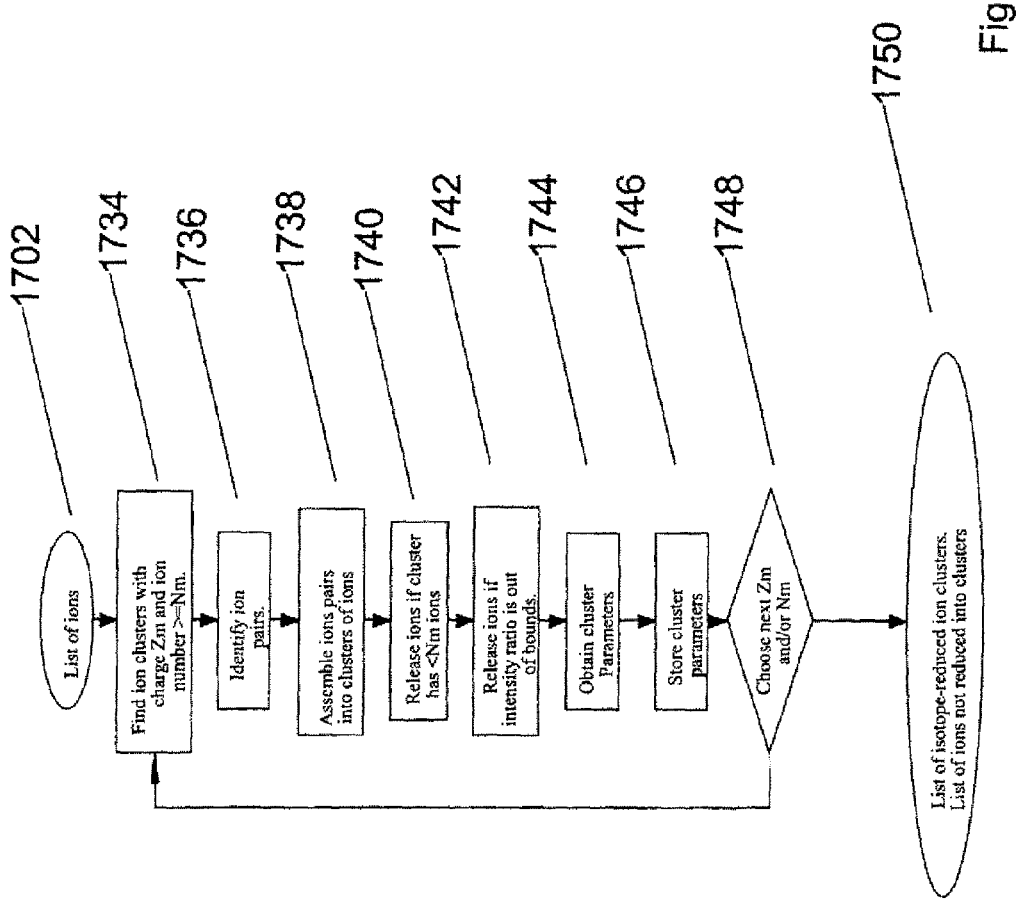
Figure 17C:
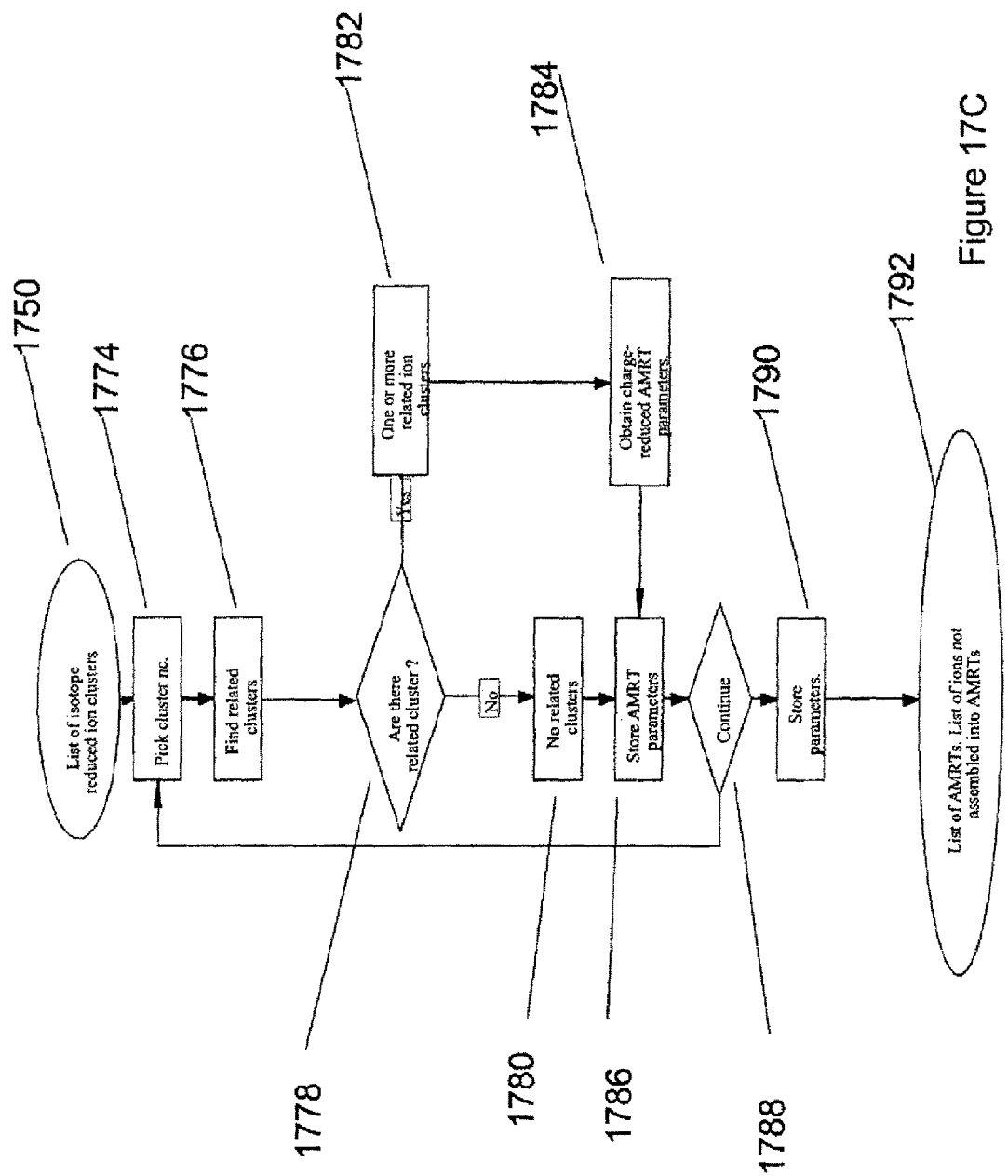

The method employed in step 306 to obtain AMRTs from ion lists is novel and described in FIG. 17A-C. FIG. 17A summarizes the method. Step 1704 takes the ion list 1702 and determines sets of ion clusters. Each ion cluster contains ions that have the same charge Z and retention time. The ion in the cluster having lowest mass is the monoisotopic ion of the peptide. This list of clusters is stored in list in 1706, and this list is input to step 1708.

Step 1708 examines the list and determines which clusters have the same retention time and mwHPlus, but different charge states. If several clusters do appear with the same retention time and mwHPlus and different charge states, then 1708 infers that these clusters must be from the same peptide. The clusters are assembled into a single set and that combined set is the AMRT for a single peptide. If a cluster appears with a unique retention time and mwHPlus, then we infer that the corresponding peptide produced only one cluster, and 1708 determines that the one cluster is an AMRT. Step 1710 stores the AMRTs and the ions not assembled into cluster. It is this combined list that is input to the PDS and EDA algorithms.

FIG. 17B shows how step 1704 identifies ion clusters from the ion list 1702. A nested iterative loop decrements two search parameters, Zm and Nm. The initial values for these search parameters are Zmax and Nmax. In each pass, Zm is the cluster charge and Nm is the minimum number of ions required to be in a cluster. For low-energy ions the initial parameter are Zmax=6, and Nmax=8. For high-energy ions these initial parameter are Zmax=3, and Nmax=8.

Step 1736 traverses all ions in the list and finds all pairs of ions that have the same retention time and are separated in m/z by 1.00335/Zm. The value 1.00335 amu is the mass difference between $^{13}C$ and $^{12}C$ isotopes. This mass difference is an approximation to the actual mass differences that occur between isotopes of the same peptide Using a mass threshold of 20 ppm (as described below), this single, approximate, value is sufficient to determine whether a pair of ions are isotopes of a common peptide.

Step 1738 assembles ion pairs into clusters. Thus if ion 7 is paired with ion 10, and ion 10 is paired with ion 15, then ion 7,10, and 15 form a cluster. If ion 15 is paired with another ion, then the cluster is expanded by that one additional ion. An ion is considered for pairing only if it is not tagged. Initially, no ion is tagged and all ions are considered. Ions are tagged in subsequent steps, as described below. Step 1738 determines all possible clusters that satisfy the pairing requirements.

The retention time requirement applied in step 1736 is determined by a retention time window and the m/z requirement applied in step 1736 is determined by a ppm window. The retention time window is 20% of the chromatographic peak width (FWHM) and is +/−0.1 minutes for a chromatographic peak width of 0.5 min (FWHM). The ppm window for at TOF with resolution of 15,000 is +/−20 ppm. That is, ions are paired only if the difference in their retention time falls within the window, and their mass difference from the m/z model described above lies within the ppm window.

In step 1738, a set of ions is recorded as a cluster and tagged provided two additional conditions are satisfied. The number of ions in the cluster must be greater than or equal to Nm, and the intensity ratios of the N=1 and N=0 ions must be within range of values expected for such ions. We define r to be the intensity ratio of the N=1 ion to the N=0, monoisotopic ion. The intensity distribution of ions in a cluster is well known and described in references cited above. In the method described here, the nominal intensity ratio r is approximated by r0=(mwHPlus/20)*0.0107. Where (mwHPlus/20) is an approximation to the number of carbon atoms in the peptide, and 0.0107 is the approximate abundance of $^{13}C$ atoms to $^{12}C$ atoms. The allowed range of intensity ratios of N=1 to N=0 ions is 40%, or r0*1.4 and r0/1.4. Thus we require that r>r0/1.4 and r<r0*1.4.

If these two rules are not satisfied, then steps 1740 and 1742 will not tag the ions, allowing them to be considered in future iterations. These rules are applied to detect and remove from consideration accidental pairings of ions from unrelated peptides.

Step 1744 obtains cluster parameters for those clusters that were obtained in step 1738 and accepted by steps 1740 and 1742. The cluster parameters are retention time, mwHPlus, intensity and charge. The retention time and mwHPlus of a cluster is that of the lowest mass ion in the cluster. The intensity of the cluster is the sum of the intensities of ions in the cluster. The charge of the cluster is the Zm parameter. If the ion cluster is accepted, 1744 tags the ions so these ions are no longer considered in subsequent iterations. Step 1746 stores the cluster parameter including the ions that form the cluster for those clusters that have been accepted.

The next iteration decrements the charge parameter Zm. Thus, in the second iteration, clusters are found that have charge Zm=Zmax−1 and have Nm=Nmax or greater ions. Continued iterations decrement Zm until Zm=1 is reached. When Zm=1 is reached, clusters of all charge states containing Nm=Nmax or more ions have been identified. After Zm=1 is reached, the next iteration resets Zm=Zmax and decrements Nmax by one, so Nm=Nmax−1. This nested iteration proceeds until Nm=2. Thus the iterations proceed from highest to lowest values for Nm in the outer loop, and highest to lowest value for Zm in the inner loop.

Step 1750 stores all clusters (cluster parameters and associated ions) found in the original ion list, and all ions not found to be in clusters.

The operation of Step 1708 is described in FIG. 17C. The list of ion clusters 1750 is looped over. Increment variable nc refers to cluster number, and nc is initialized to 1. Step 1776 finds all clusters that have the same retention time and mwHPlus as cluster nc. If step 1778 determines there are no such other clusters, then step 1780 notes that cluster nc is an AMRT and stores it parameters in step 1786. Thus, at a given retention time, if there is only one cluster with a given mwHPlus value, than cluster is considered to be an AMRT of a peptide. That is there is a peptide that appears as a single cluster. That AMRT is added to AMRT list. The AMRT parameters are the same as the cluster parameters.

If step 1778 determines that one or more clusters have the same retention time and mwHPlus as cluster nc, then step 1782 notes that this set of clusters are an AMRT. Step 1784 assembles these clusters into a single AMRT and obtains their parameters, and 1786 accumulates the result. That is, if there are multiple clusters having the same mwHPlus, we infer that a peptide is in the data that has ions that appear in these different charge and isotope states. The AMRT parameters are retention time of the most intense cluster, mwHPlus of the most intense cluster, intensity is the sum of intensities of all clusters, and the fractional charge state is the sum of charges of clusters weighted by fractional intensity of each cluster.

The retention time requirement applied in step 1778 is determined by a retention time window and the m/z requirement applied in step 1778 is determined by a ppm window. These parameters are obtained and applied in the same fashion as in the case of the ion pairing determination, described above.

When all clusters are looped over, the loop terminates, and all results are stored. The final result is the AMRT list containing all AMRT parameters and the ions associated with those AMTS, as well as those ions that were not part of cluster. It is this final list that is input to the PDS and EDA algorithms.

The other input to the PDS and EDA algorithms are sequences of target peptide precursors and their fragment sequences. FIG. 3B is a flowchart for a method of selecting target precursor peptides using a selected database of protein sequences. In step 310, an appropriate database is selected. Preferably, the database contains protein sequences corresponding to all possible proteins that are present or likely to be present in the sample. In the database, each protein is described by its primary sequence of amino acids. From such a sequence it is possible to predict the peptides that will result from a digestion protocol as well as other properties such as hydrophobicity and charge state. For example, tryptic digestion cleaves sequences at the known amino acids K and R. Based on these cleavage products, the Y- and B-ion fragments and corresponding masses that result from collisional fragmentation can be predicted. Thus, the database provides a model of the masses and other physical attributes that can occur in the low- and high-energy spectra.

During protein identification the AMRTs or ions seen in the data are compared with the masses contained in the database to effect a reliable identification of the peptides present in the acquired LC/MS data. Ideally, all database peptides that are in the data are identified without error.

In step 312, in-silico digestion is performed on one or more of the protein sequences in the database to generate precursor peptides in the database. In-silico digestion is a synthetic digestion based on known digestion properties, such as described above. In step 314, the exact mass of the precursor peptides is determined by looking at the amino acid sequences making up the precursor peptides. The exact masses and sequences corresponding to the precursor peptides are stored for subsequent use.

FIG. 3C is a flowchart for a method for identifying peptides in a mixture according to an embodiment of the present invention. The method begins with selection of a precursor peptide (target precursor) from the database. Using the selected database peptide, the masses of the Y- and B-ion fragments corresponding to the selected peptide are determined, or obtained from the database. In this manner, a list of masses is assembled. This list of masses includes masses corresponding to each of the Y-ions, B-ions (possibly excluding the lowest mass Y- and B-ions), as well as the unique mass associated with the unfragmented precursor itself.

Other precursor masses and fragment masses might be considered, such as those corresponding to chemical modifications to the precursor peptide. Examples of such modifications are those due to glycocylation or phosphorylation. Other fragment mass might be considered such as fragmentation at peptide bonds other than the Y or B bond.

Both the low and the high energy AMRTs from the LC/MS and LC/MS$^E$ data are then searched for each mass on this list. Matching masses, or hits, occurs when a mass from the database (precursor or fragment) lies within a mass search window of a mass measured in the data (at low-energy or at high-energy). All AMRTs that are hit are recorded together with their mass, retention time, and intensity. Matching masses, or hits, are accumulated for each of a plurality of retention time bins. A bin having an accumulation greater than a detection threshold is deemed to be associated with the target precursor.

As described below, the method makes critical use of retention time alignment of the AMRTs seen at low and at high-energy. Also, as described below, the method can identify AMRTs in the data that are related to, but not identical to the peptides in the database. Such identification can be made when there is a significant overlap of masses associated with the peptide fragments from the database with masses of AMRTs found in the data at substantially identical retention times.

Referring to FIG. 3C, in step 350 a precursor peptide (e.g., a tryptic peptide) is selected from the in-silico digestion peptides. This peptide, alternately referred to as a target sequence or a target precursor, is described by its mass (mwHPlus) and the masses (mwHPlus) of its Y- and B-ions in step 352. Any peptide in the database can be selected as the target precursor in step 350.

A list of exact masses of the target sequence and its Y- and B-ions is determined in step 352. In step 354, the masses of the target, precursor sequence and its Y- and B-ions are used to search for all AMRTs in the data in the high- and low-energy lists that have mwHPlus's within a search tolerance (e.g., 20 ppm). In step 356, AMRTs that match a mass in the mass list from the database to within a search tolerance are noted, tagged, or otherwise identified. The search tolerance can be user-specified or automatically determined from the data by known statistical means. An automatic method for determining the mwHPlus tolerance is described below.

Ideally, low-energy spectra contain only precursor ions. In practice, precursor ions can fragment in the ion source, so as a result, low-energy spectra can contain fragments ions of precursors. Such ions are referred to as in-source fragments, and generally appear at attenuated intensity.

Ideally, high-energy spectra contain only fragment ions. But in practice, collisional fragmentation of precursor ions may not be complete, so as a result, high-energy spectra can contain precursor ions. Generally such precursor ions appear at intensities in the high-energy mode that are attenuated relative to their intensity in low-energy mode.

Thus, a precursor or fragment mass may appear in either the low-energy or the high-energy data or both. If a mass in the list appears in the low-energy AMRT data the PDS algorithm notes, tags, or otherwise identifies as appearing in that data in that mode. If a mass in the list appears in the high-energy AMRT data the PDS algorithm notes, tags, or otherwise identifies as appearing in that data in that mode. Thus, the present invention makes use of all ions derived from a common precursor molecule, regardless of the mode in which such ions are produced or detected.

In step 358 a detection chromatogram is formed. Assuming that a sequence is present in the data with ions at detectable levels, all such ions will be tagged in the search carried out in step 356. However, many other ions not corresponding to the sequence will also be tagged. The detection chromatogram shows the number of ions (both at low- and high-energy) that are tagged within a retention time interval, for each retention time, where the vertical signal is the number of tags observed in the retention time interval. The effect of false positives tags is to produce baseline noise.

According to one embodiment of the present invention, the detection chromatogram is a simple histogram. The histogram is a series of bins, the center of each bin corresponding to a retention time and the width of the bin corresponding to a retention time interval. The histogram is formed by simple one up counting for each hit the bin corresponding to the particular retention time interval that contained the retention time of the mass that was hit.

Figure 14:
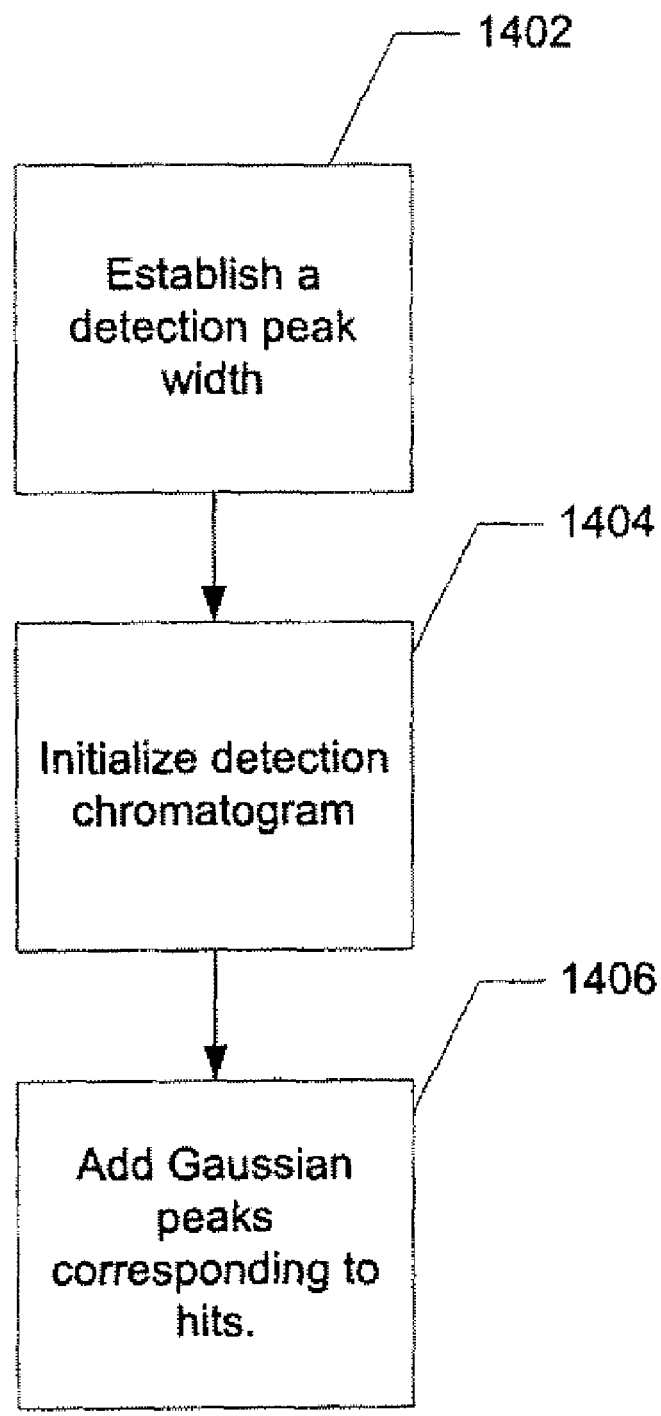
FIG. 14 is a flow chart for a method of generating the detection chromatogram using addition of detection Gaussian peaks.

According to a second embodiment of the present invention, the detection chromatogram is derived using accumulated Gaussian-shaped peaks. In the second embodiment of the present invention, each AMRT hit is represented by a Gaussian-shaped peak in the detection chromatogram. FIG. 14 is a flow chart for a method of generating the detection chromatogram according to the second embodiment.

In step 1402, a detection peak width is established. The detection peak width is the width of a Gaussian-shaped peak that is added to the detection chromatogram for each hit. The width of the added Gaussian peak (henceforth referred to as the detection Gaussian, or detection Gaussian peak) is set to a specified fraction of the FWHM of a chromatographic peak in the data. According to an embodiment of the present invention, the fraction is 10%. Thus if the FWHM peak width of a typical chromatographic peak is 0.5 minutes, the FWHM of the detection Gaussian is 0.05 minutes.

The time range of the detection chromatogram corresponds to the time range of the separation. If the FWHM peak width of a typical chromatographic peak is 0.5 minutes, for example, the sample period of the detection chromatogram is chosen to be about 1% of that width, or 0.005 minutes. In step 1404, the detection chromatogram is initialized. The initial values of all points in the detection chromatogram are set to zero. The list of AMRTs that are hit (those found in step 350) are traversed (looped over).

In step 1406, detection Gaussian peaks corresponding to hits are added. This is done by analyzing all low and high-energy AMRTs that were hit. For each low- and high-energy AMRT that was hit, a single detection Gaussian of unit height (having width of the detection peak width) is added to the detection chromatogram at the AMRT's or ion's respective retention time.

If two AMRTs having different masses elute at the same time, their detection Gaussians will sum to a peak having a peak height of 2. If N AMRTs having different masses elute at the same time, their detection Gaussians will sum to a peak having a peak height of N.

The width of the detection Gaussian corresponds to the standard error with which the retention time of a peak is measured. A method for determining the standard error in the measurement of retention time is described below.

Referring back to FIG. 3, in step 362, the local maxima of the detection chromatogram are identified. A peptide detection threshold is determined. The peptide detection threshold determines if a peptide has been identified. Methods by which a detection threshold can be determined are specified below. For example, the peptide detection threshold might be chosen to be 4 AMRTs. Thus, a peptide is deemed identified if at least 4 AMRTs are present in the same retention time window.

AMRTs detected in both the low-energy or high-energy spectra can contribute to this count.

That is, in step 362 a target peptide in the database is determined to be present in the data if (A) more than the threshold number of AMRTs are found, (B) the relative retention times of the AMRTs are within +/−0.05 min, and (C) the mwHPlus values of the AMRTs all lie with in 20 ppm of fragment molecular weights and precursor molecular weights in the selected peptide database. In an embodiment of the present invention, the detection chromatogram is constructed so that if (A) is true, then those masses that contribute to the local maximum must also satisfy (B) and (C). The PDS algorithm to this point identifies AMRTs that if present, satisfy this condition and thereby indicate that the selected precursor (target precursor) is present.

Any and all local maxima above the detection threshold indicate either that the selected peptide is in the data, or that a peptide is in the data that is closely related to the selected peptide. As used in this context, the term "closely related to" means that there is significant sequence correspondence between the database peptide and the peptide found in the data at the retention time $t_r$. Note that such detection can be made whether or not an AMRT having the precursor molecular weight (mwHPlus) is found. Thus, one or more retention times can be found.

Figure 15:
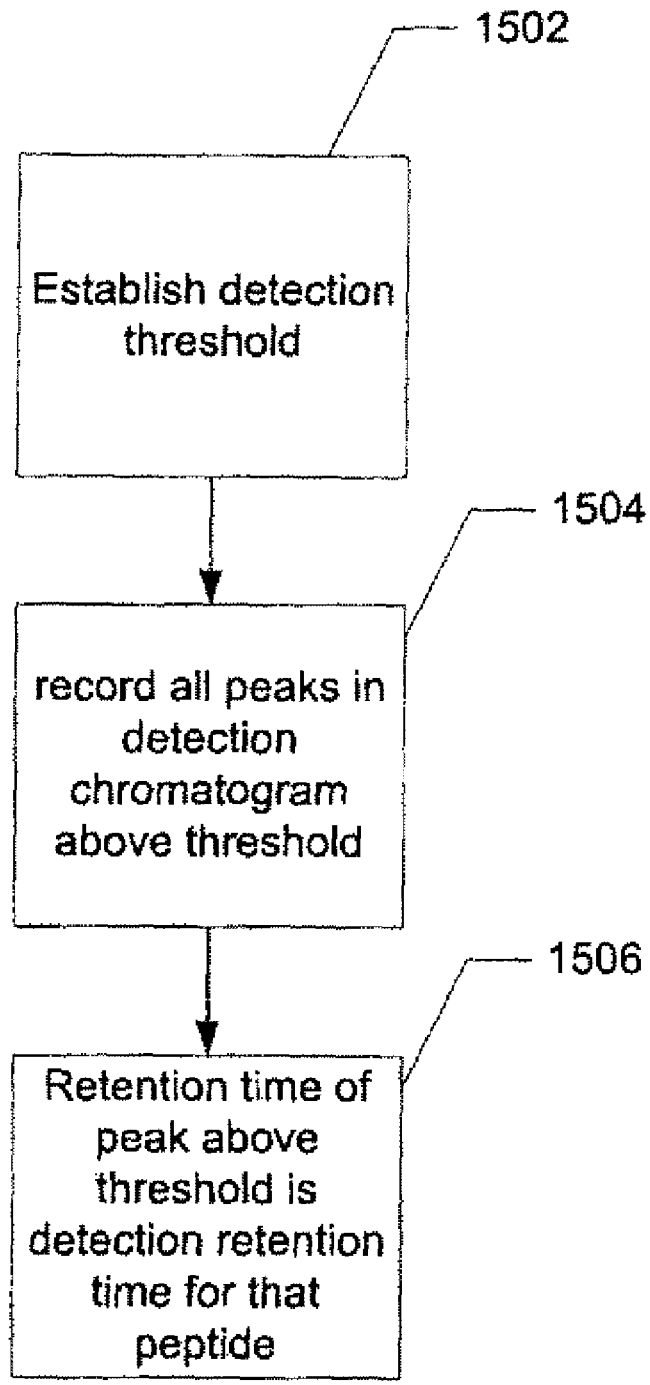
FIG. 15 is a flowchart for a method for identifying sequence identifications and their retention times according to an embodiment of the present invention.

FIG. 15 is a flowchart for a method for identifying sequence identifications and their retention times that can be employed in step 362 according to an embodiment of the present invention. Upon completing the method illustrated in FIG. 15, the target precursors found in the low-energy, LC/MS data will have been identified, as well as those precursors found in the low-energy, LC/MS data whose sequence is related to (but not identical with) that of the target precursor.

In step 1502 a detection threshold is established. The detection threshold can be determined from all the local maxima found in the detection chromatogram. Each local maxima in the detection chromatogram has a value. From these values, a median value is obtained. The detection threshold is typically set to about 4 times the median value. This detection threshold corresponds to a maximum number of fragments that would be likely to fall within a detection peak width by chance alone. Typical values for the detection threshold vary between 5 and 10 fragment ions per detection peak width of 0.05 minute.

In step 1504, all peaks in the detection chromatogram above the threshold are recorded. A peak will not be detected in the detection chromatogram if the target peptide (or a peptide with a sequence related to that of the target) is not present in the data. If, on the other hand, the target peptide, or a peptide with a sequence related to that of the target, or both, are present at sufficient concentration, then there can be one or more local maximum values above the detection threshold.

In step 1506, the retention time of the detection peak above the threshold is taken as the retention time of that peptide. The value for that retention time at which the target peptide (or sequence-related target peptide) was detected is $t_d$. The height of the detection chromatogram gives the approximate number of ions detected for the target peptide (or sequence-related target peptide) and the location of the local maximum in time is the retention time at which the target peptide (or sequence-related target peptide) eluted from the chromatographic column.

Referring back to FIG. 3, in step 364, the low- and high-energy AMRTs for each identification are collected. These AMRTs are collected by the following rule: given the value $t_d$ from the detection chromatogram for the elution time of the peptide, all AMRTs that are on the hit list and are within the detection width, +/−0.05 minutes of $t_d$ in our example are noted, tagged, or otherwise collected. Thus these collected AMRTs then satisfy two conditions (A) the relative retention times of the AMRTs are within +/−0.05 min of $t_d$, and (B) the mwHPlus values of the AMRTs all lie with in 20 ppm of fragment molecular weights and precursor molecular weights in the selected peptide database.

The number of AMRTs collected by this rule will be close to, but not necessarily exactly the same as the height of the detection chromatogram at $t_d$. AMRTs associated with the peptide may have slightly different retention times, due to measurement error, so the detection Gaussian peaks may not exactly align. The height of detection peaks in the detection chromatogram that are above the detection threshold can be other than an integer if the retention times of the AMRTs do not have the same values. However, the number of AMRTs collected by the above rule must obviously be an integral value.

In step 366, the collected AMRTs are stored. The spectrum of the collected AMRT can be displayed if desired. In step 368, the search is repeated for the next precursor peptide if desired, by returning to step 350. If the search is not to be repeated, further analysis can be performed in step 370. Such further analysis can be displaying the result, combining the results with results from other injections or quantitating the identified peptide.

Combining results from other injections can consist of comparing the retention times at which the same peptide appears in two or more injections. Combining results from other injections can consist of comparing the intensities of the corresponding AMRTs found in two or more injections. These injections could be replicate injections of the same mixture, or injections of two samples taken under different conditions.

The retention times and intensities from replicate injections can be compared for consistency to further confirm the correct identity of the peptides. If the injections are from different samples (or conditions), the retention times can be compared for consistency to further confirm the correct identity of the peptides, and the intensities can be compared, or ratioed, to reveal changes in amount of the peptide in the sample between the two conditions.

Rules can be applied to the list of peptide identification to infer which proteins were present in the original sample.

Figure 16:
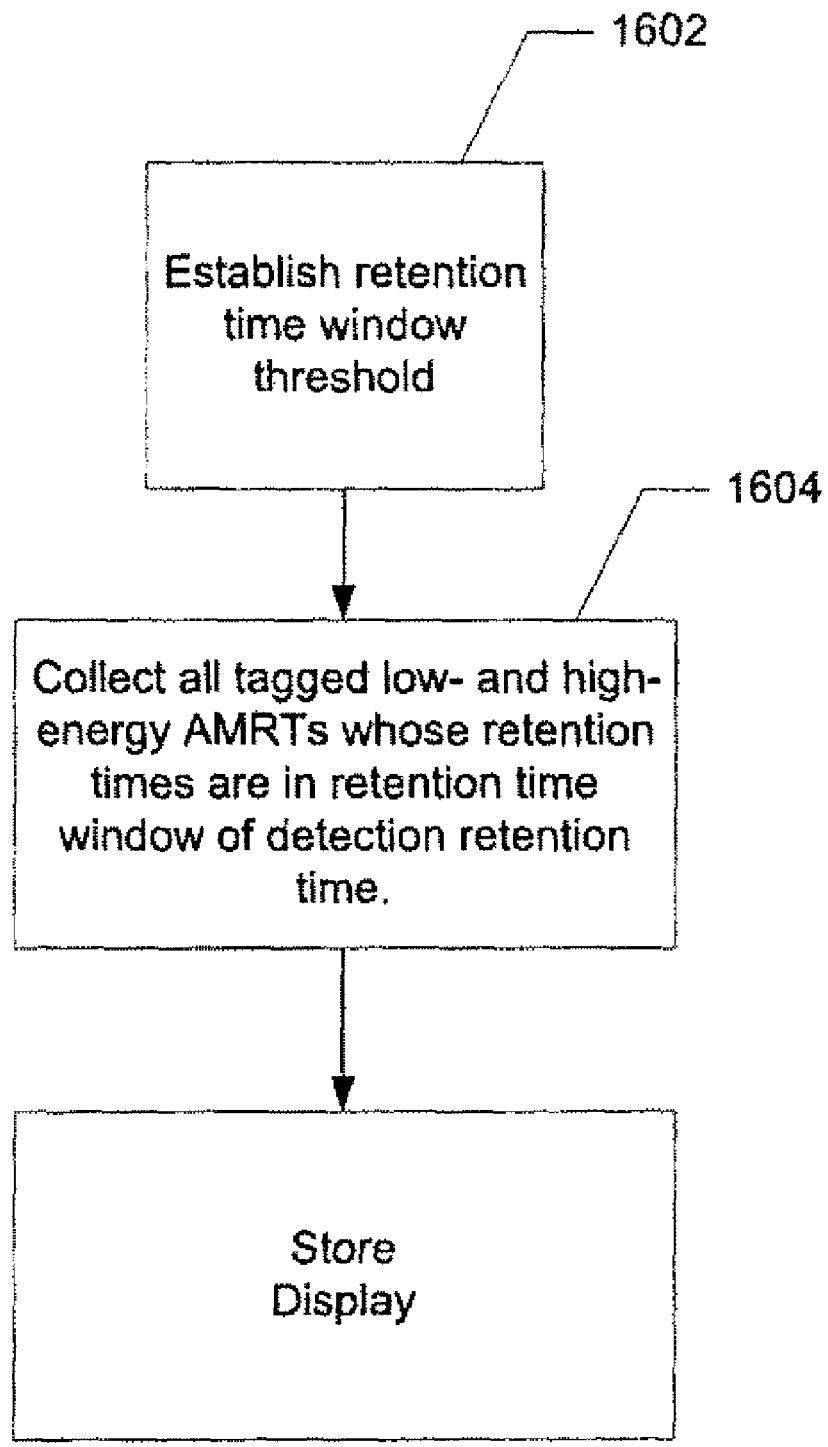
FIG. 16 is a flowchart for collecting AMRTs and ions associated with each sequence identification according to an embodiment of the present invention.

FIG. 16 is a flowchart for collecting AMRTs and ions associated with each identified sequence. In step 1602, a retention time window is established. Generally, the retention time window is set equal to the detection peak width, which is +/−0.05 min in the example above. In step 1604, all tagged low- and high-energy AMRTs whose retention times are within the retention time window threshold centered on the detection retention time $t_d$ are collected. The detection peak gives the retention time for the elution of the peptide. The ions whose retention times are within the retention time window threshold centered on the detection retention time $t_d$ are the ions detected for that peptide. That collection of ions contains all ions or AMRTs that were hit at low-energy and high-energy. These ions may or may not contain the mass corresponding to the target precursor.

The results are the ions found in the retention time window centered on the apex of the detection peak. These ions have masses that correspond to the peptide fragment masses and will generally include, but not always, the mass of the target precursor. In step 1606 the results are stored on a storage device. In addition, in step 1606 the results can be displayed to a user.

Figure 4A:
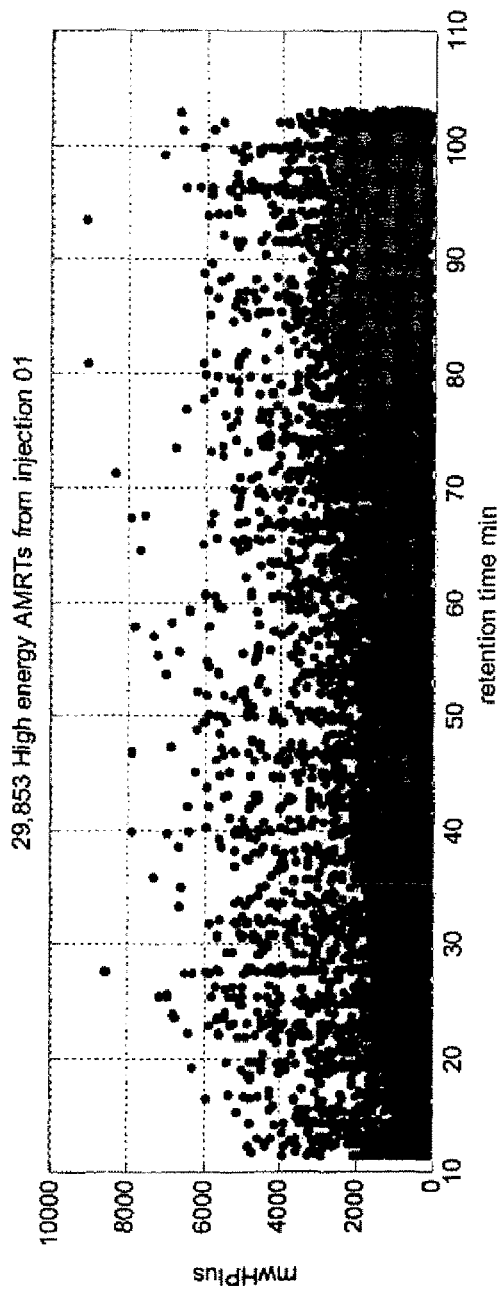
FIG. 4A is an exemplary plot showing all AMRTs found at high energy.
Figure 4B:
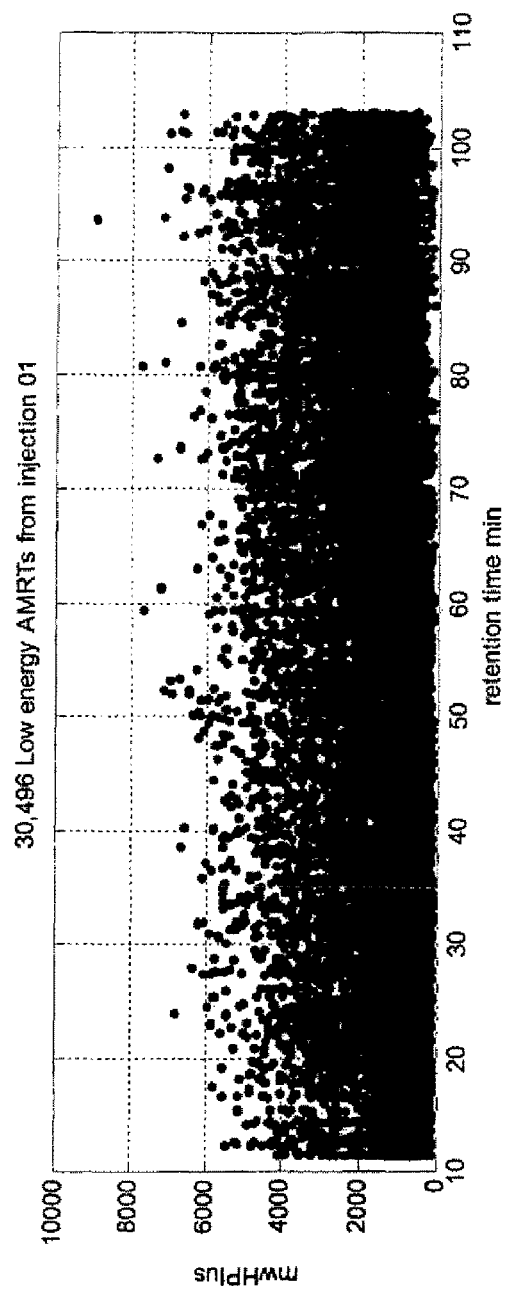
FIG. 4B is an exemplary plot showing all AMRTs found at low energy.
Figure 4C:
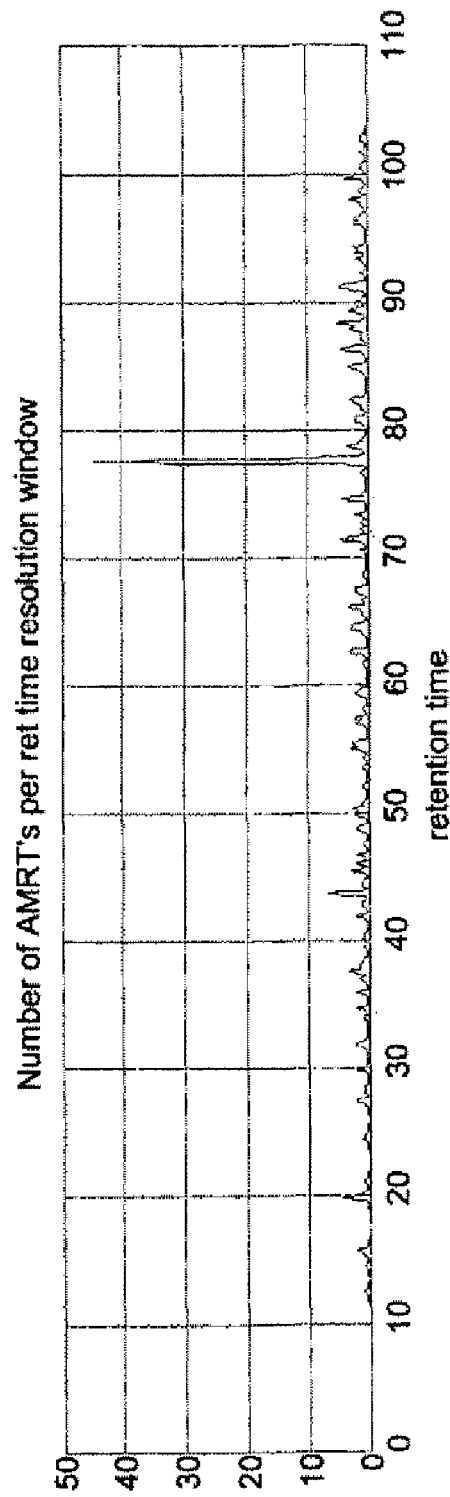
FIG. 4C is an exemplary detection chromatogram derived from the data shown in FIGS. 4A and 4B showing the number of hits per retention time for a given theoretical peptide from a database.

FIG. 4A is an exemplary plot showing all AMRTs found at high energy. FIG. 4B is an exemplary plot showing all AMRTs found at low energy. In FIGS. 4A and 4B, the vertical axis is the mwHPlus of the AMRT and the horizontal axis is retention time. FIG. 4C is an exemplary detection chromatogram derived from the data shown in FIGS. 4A and 4B showing the number of hits per retention time corresponding to precursor and fragment masses for a given peptide sequence. FIG. 4C clearly illustrates a peak in hit occurrence near approximately 78 minutes. This peak contains a precursor peptide found in the data. The distribution observable in FIG. 4C indicates the noise background against which the significance of the peak in hit occurrence can be judged.

Figures 5A, 5B, 5C:
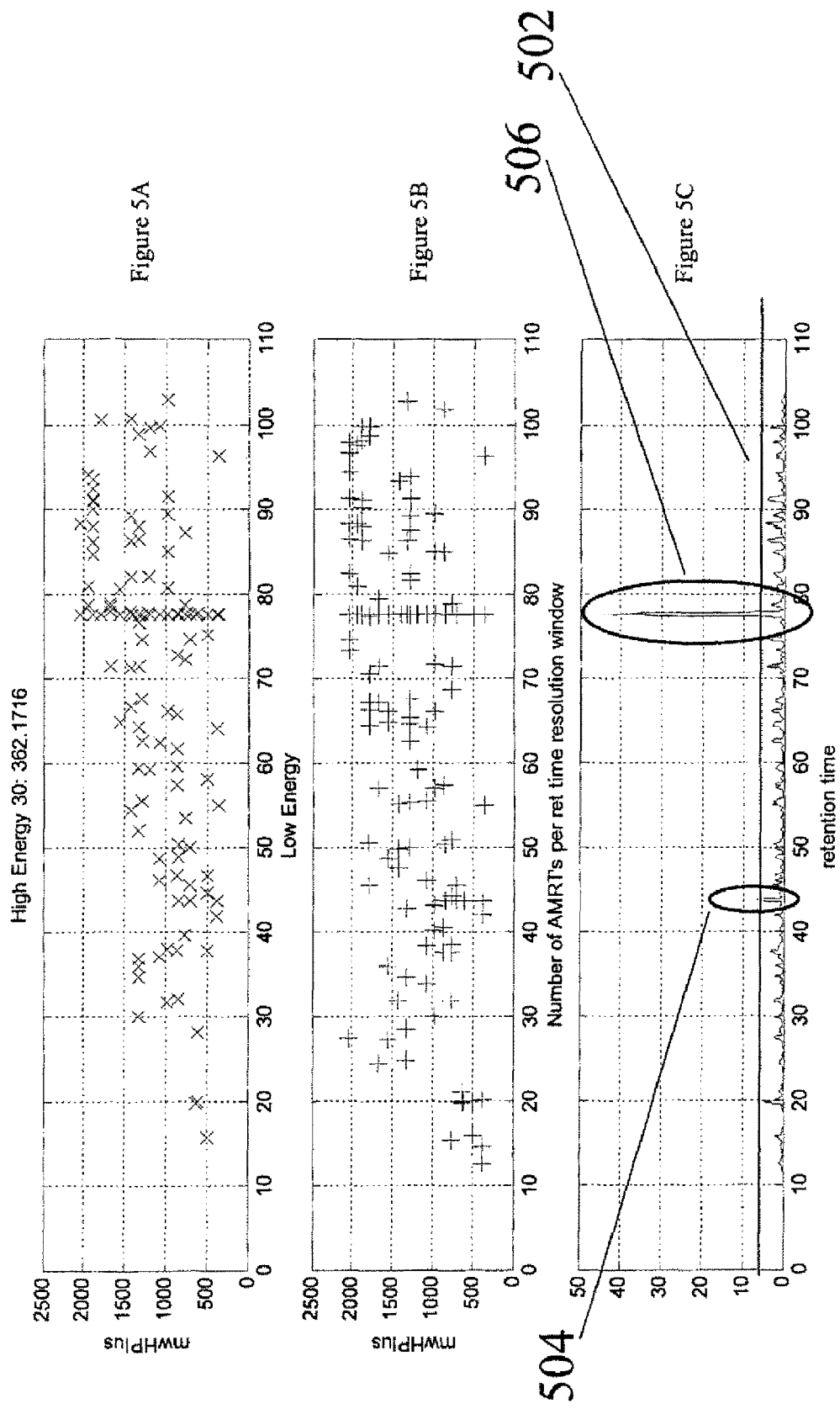
FIG. 5A is an exemplary plot showing only hits of AMRTs in the high-energy plot of FIG. 4A.
FIG. 5B is an exemplary plot showing only hits of AMRTs in the low-energy plot of FIG. 4B.
FIG. 5C is a histogram plot of the hits in the high and low energy plots of FIGS. 5A and 5B.

FIG. 5A is an exemplary plot showing only hits of AMRTs in the high-energy plot of FIG. 4A corresponding to precursor and fragment masses for a given peptide sequence. FIG. 5B is an exemplary plot showing only hits of AMRTs in the low-energy plot of FIG. 4B corresponding to precursor and fragment masses for a given peptide sequence. FIG. 5C is a histogram plot of the hits in the high- and low-energy plots of FIGS. 5A and 5B corresponding to precursor and fragment masses for a given peptide sequence. FIG. 5C is an exemplary detection chromatogram similar to FIG. 4C, but adding a threshold 502. Threshold 502 indicates the number of hits required to indicate the presence of a peptide. A clear sequence-related precursor peptide 506 is identified at a retention time of approximately 78 minutes, where more than 40 hits are counted. A possible sequence-related peptide 504 is identified at a retention time of 43 minutes. The hits of low-energy AMRTs to fragment masses are evidence of in-source fragmentation. In-source fragmentation of precursor ions results in the fragment ions seen in low-energy spectra.

Peak characteristics can be used to further assist in peptide identification. One such characteristic is peak shape. All chromatographic peaks related to the same precursor peptide must have the same peak shape and peak width. However, chromatographic peaks related to different peptides may not have the same peak shape and width. Consequently, it is possible for two peptides to elute at the same chromatographic retention time, but have different peak shapes and/or widths. Thus, peak shape can be used to reject coincidences that might otherwise lead to false identifications. This property of peak shape can also be used to reduce the threshold that is, the number of ions required to align at the same retention time to indicate the presence of a target peptide. Similarly, peak shape can confirm the relationship between the AMRTs.

Even though all chromatographic peaks related to the same precursor peptide must intrinsically have the same peak shape and peak width, variations in such peak shapes or width may be observed to occur due to measurement error. Another source of variance is interference by other peaks unrelated to the precursor.

Figure 6A:
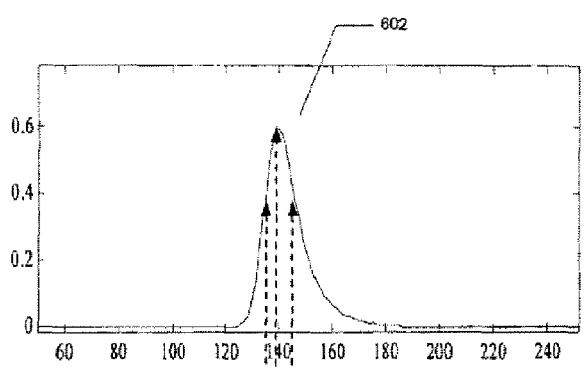
FIGS. 6A-B illustrate how the zero crossing of the $2^{nd}$ derivative of a chromatographic peak can be obtained.
Figure 6B:
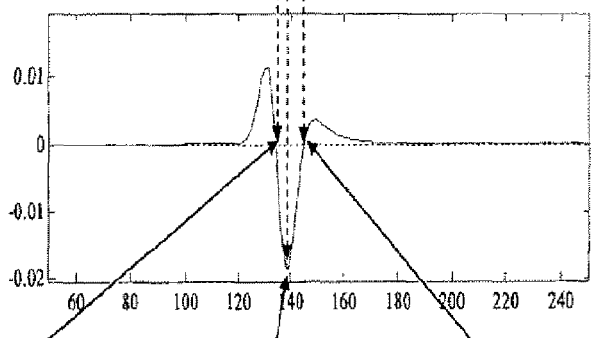

As shown in FIG. 6A-B, there are several times on peaks that can be compared to determine peak width and peak shape. These include the apex time (retention time), the times of the up slope inflection point and the time of the down slope inflection point. Inflection points can be obtained from the times of the zero crossings of the $2^{nd}$ derivative of the peak shape. The $2^{nd}$ derivative can be obtained via a Savitzky-Golay or related polynomial filter. FIG. 6A illustrates an exemplary chromatographic peak 602. FIG. 6B illustrates plot the second derivative of chromatographic peak 602. The times of the apex 604 and inflection points 606a and 606b of the $2^{nd}$ derivative trace are indicated. These times that can be compared to compare peak shape and width. For reference, the points on the peak in the top plot corresponding to the times found in the bottom plot are indicated by the dashed lines.

The time difference between the down slope and up slope inflection points measures the peak width. For a Gaussian chromatographic peak, this width is 2 times the Gaussian standard deviation. The ratios of heights of the peaks at the up and down slope inflection points are an additional measure of peak asymmetry or peak shape. The magnitude of the time difference between the apex time and the up and down slope inflection times are other measures of peak width. The ratios of these times are a measure of peak shape or asymmetry.

Taking peak shape into account, additional processing of the detection chromatogram can be performed. As described above, the local maxima of the detection chromatogram are found. The shapes and widths of the peaks that align during that local maximum are compared. A peak is rejected if its width or shape is an outlier.

Figure 7:
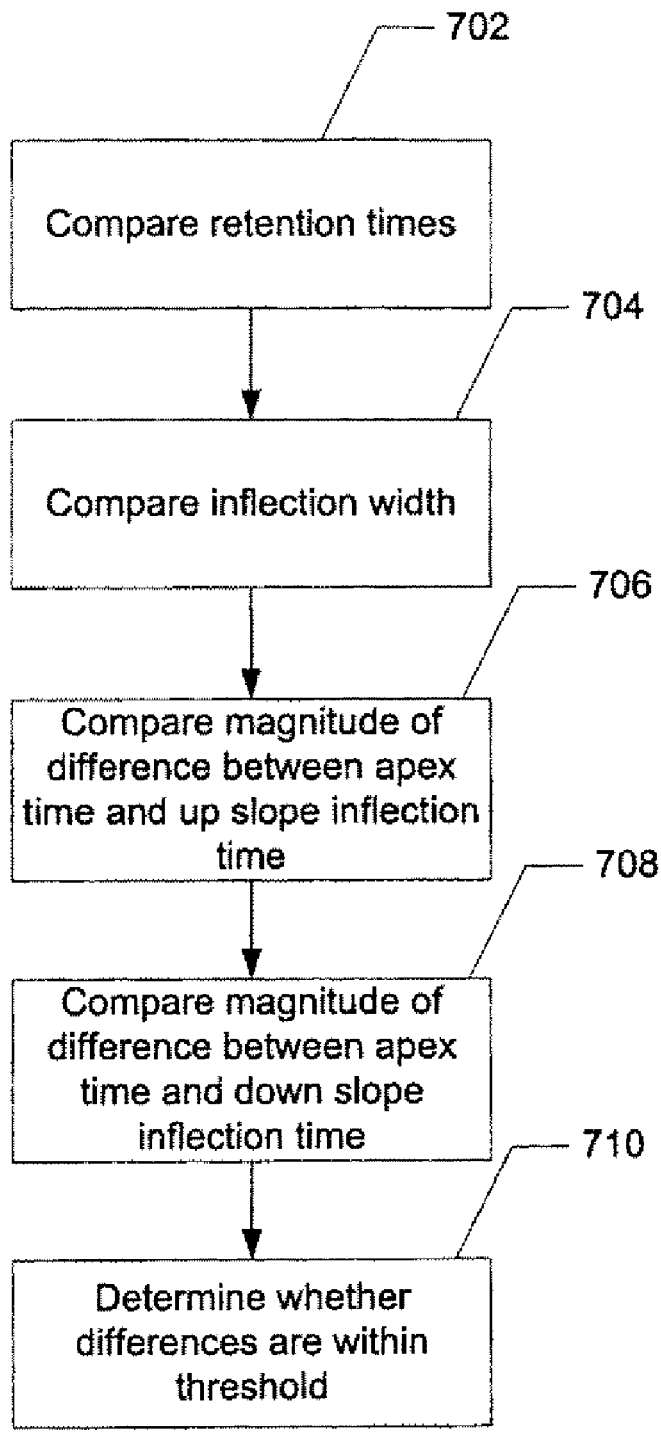
FIG. 7 is a flowchart for a method for comparing peak shape and peak width according to an embodiment of the present invention.

FIG. 7 is a flowchart for a method for comparing peak shape and peak width according to an embodiment of the present invention. In step 702, the retention times of the peaks are compared. In step 704, the inflection widths of the peaks are compared. The inflection width of a peak is the time between its inflection points. For example, the time between inflection points 606a and 606b in FIG. 6A-B is the inflection width of peak 602. In step 706, the magnitude of difference between apex time and up slope inflection time is compared. In step 708, magnitude of difference between apex time and down slope inflection time is compared.

In step 710, the times are analyzed to determine if they fall within a time threshold. In an embodiment of the present invention, the time threshold for each of the comparisons is the detection width of 0.05 minutes. Thus, all of the time comparisons must fall within 0.05 minutes for the peaks to be considered as corresponding to the same peptide. This threshold can be user-specified or statistically determined. The user-specified or statistically-determined threshold can be an absolute time or a fraction of the peak width.

The preferred peak used for comparing peak shapes and sizes is the $^{12}C$ monoisotopic peak of a cluster of ions associated with a peptide. The $^{12}C$ monoisotope is the lowest mass peak where all isotopes are in their most abundant state. Other peaks in the peptide cluster of ions can be used as well. Further, averages of retention times and up and down slope inflection times can be used for the peak shape and width comparisons.

In a second embodiment of the present invention, ions, corresponding to precursors, fragments and their isotopes, are searched instead of, or in addition to, searching AMRTs. An advantage of using ions is that for low-intensity peptides, the peptide might appear as a single ion. For example, when using AMRTs, at least two ions are needed to detect an AMRT and establish its charge state.)

Figure 10:
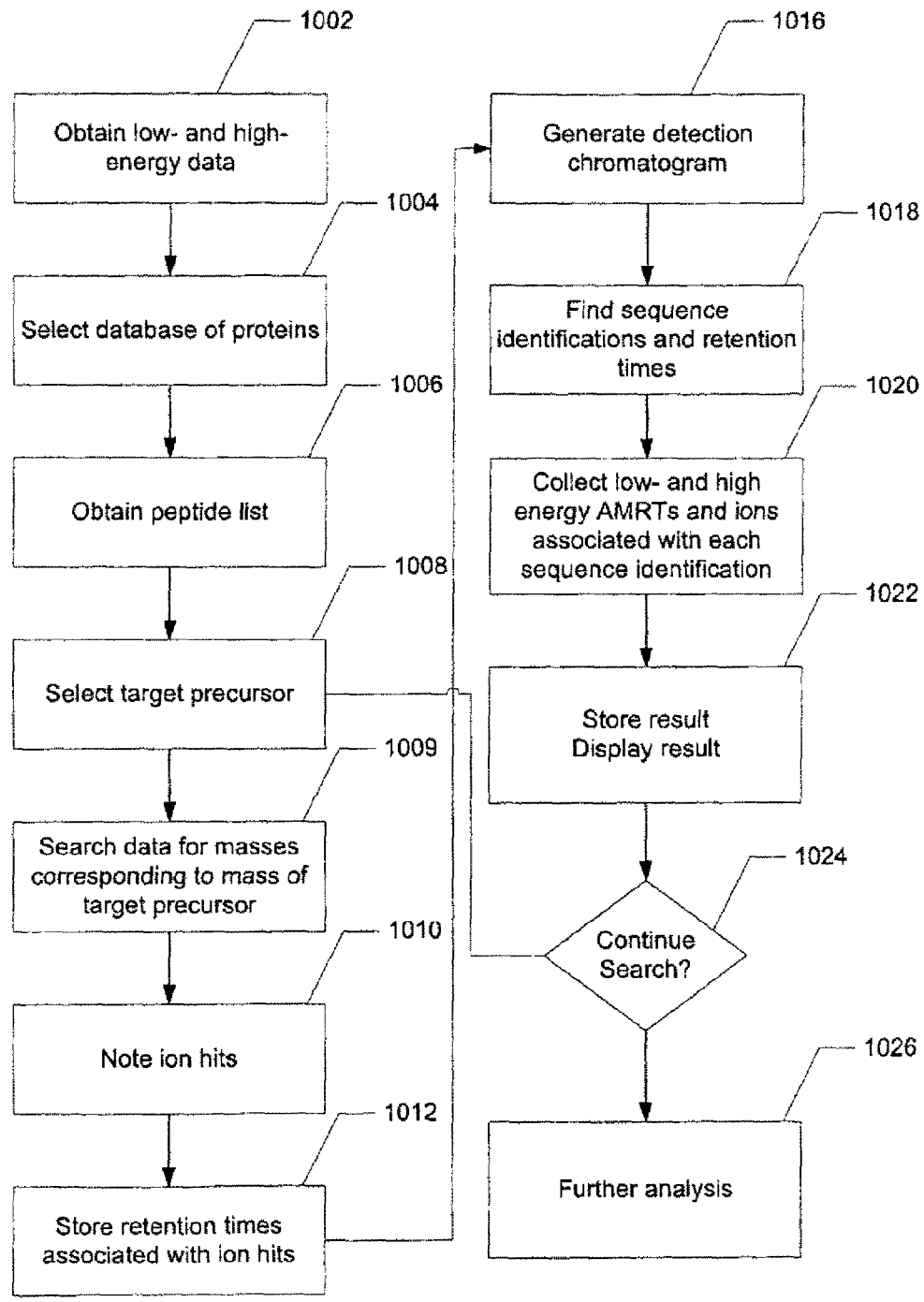
FIG. 10 is a flowchart for a method for identifying peptides in a complex mixture using ions according to an embodiment of the present invention.

The ion-based search is similar in many respects to the AMRT search described above. FIG. 10 is a flowchart for a method for identifying peptides in a complex mixture using ions according to an embodiment of the present invention. A summary of the steps in the PDS algorithm using ions follows.

In step 1002, low-energy and in high-energy ions are obtained from a single injection of a peptide mixture. The peptide mixture is generally obtained from a digest of a protein sample. The low- and high-energy data are obtained using a high-voltage/low-voltage switching technique as described above. In step 1004, a database of proteins is selected. In step 1006, a list of peptides corresponding to the proteins in the database is obtained using rules for peptide digestion.

In step 1008, a target precursor is selected from the database (e.g., a tryptic peptide). This peptide is described by its mass (mwHPlus) and the masses (mwHPlus) of its Y- and B-ions. In step 1009, data is searched for masses corresponding to the mass of the selected precursor. Given these masses, in step 1010 all ions in the data in the high- and low-energy lists that have masses within a search tolerance. (e.g., within 20 ppm) are noted. When using ions as the search criteria, the search must be over multiple charge states and isotope numbers. The charge states are generally restricted from 1 to 3 for high energy fragments. The charge states are generally restricted to 1-6 for low energy.

In a preferred embodiment of this ion-based search, the charge states of all ions obtained from the low-energy spectra are assumed to be $Z=2$, and the charge states of all ions obtained from the high-energy spectra are assumed to be $Z=1$. These assignments are made because $Z=2$ is the most commonly observed peptide charge in low-energy, and $Z=1$ is the most commonly observed peptide charge in high-energy. In addition, the isotope number of all ions are assumed to be $N=0$, that is all ions are assumed to be in their monoisotopic state. These charge state and isotope assignments are needed to determine mwHPlus value for the respective ions. It is these mwHPlus values that are then compared against the masses obtained from the database in step 1009, as described below.

The retention time of each ion hit is recorded in step 1012. The output at this stage is a list of ions from the high and low energy data that are hit by a mass from database peptide.

A synthetic, detection chromatogram is generated in step 1016 in as described above. In an embodiment of the present invention, each ion hit is represented by a detection Gaussian peak, as follows. The time range of the chromatogram corresponds to the time range of the separation. If the FWHM peak width of the chromatogram is 0.5 minutes, for example, in an embodiment of the present invention, the sample period of the detection chromatogram is chosen to be about 1% of that width, or 0.005 minutes. The initial values of all points in the detection chromatogram are set to zero. The list of ions that are hit are traversed (looped over). For each entry in the list, a Gaussian-shaped peak (detection Gaussian peak) is added to the detection chromatogram. The width of the detection Gaussian peak is set to a specified fraction of the FWHM of a chromatographic peak in the data. In an embodiment of the present invention, the fraction is 10%. Thus, the FWHM of the detection Gaussian is 0.05 minutes. The width of the detection Gaussian peak corresponds to the standard error with which the retention time of a peak is measured.

If two ions that have different masses elute at the same time, their detection Gaussians will sum to a new peak that has a peak height of 2. If N ions that have different masses elute at the same time, their detection Gaussians will sum to a new peak that has a peak height of N.

Steps 1018-1026 are similar to steps 362-370 of FIG. 3C described above. The local maxima of the detection chromatogram are found in step 1018. The threshold is determined. Methods by which a detection threshold can be determined are specified below. A possible value for the threshold is $>=4$ ions present (obtained by summing AMRTs at low with those at high energy) within the same retention time window.

All local maxima above the detection threshold indicate the presence of a peptide in the data that either is identical to the database peptide or closely related to it. The local maximum determines the retention time of the detection. The retention time that contains a significant number of ions is an indication of that the target peptide is present in the data. Given this retention time, all ions at both low and high energy that lie with in a threshold value of this retention time, and within a threshold value of the mass are selected in step 1020. An additional threshold can be applied to determine the number of ions that meet these requirements. Groups of ions that are above threshold are recorded in step 1022. These groups indicate peptide identifications. In step 1024 if there are additional precursors, the search is then repeated for the next precursor peptide, by returning to step 1008. Further analysis of the results can be performed in step 1026.

When generating the detection chromatogram, an additional requirement may be imposed that the $^{12}C$ ion be seen for each charge and isotope cluster, for any related ion to be included as a hit. That is, if the $^{13}C$ is seen it is not counted unless the $^{12}C$ in the same charge state is seen.

The above described PDS algorithm has a number of advantages over conventional peptide identification methods. One of the problems with the prior art is that it assumes that AMRTs (or ions) in low-energy are only precursor peptides. However, fragmentation can occur in low-energy (in-source fragmentation) as a part of the ionization and focusing process. Thus, in conventional system, a search can be initiated by an AMRT that is not in fact a precursor. Such a search either will not result is a hit to a target, or a hit to a target will occur resulting in a spurious, false identifications. Such false identifications are referred to as false-positives.

Using embodiments of the present invention however, as can be seen in FIG. 5B for example, in-source fragments that appear at low-energy are detected. Because embodiments of the present invention detect AMRTs in low- and high-energy data, all the AMRTs in low-energy that are in fact fragments (not tryptic precursors) are identified.

Another advantage of embodiments of the present invention is that searches can be performed and identifications of peptide sequences can be made without requiring the detection of the precursor mass. That is, the peptide from the database may have a precursor molecular weight (mwHPlus) of M. In conventional methods, the search is initiated by looking for peptides in the database with molecular weight (mwHPlus) of M. If the database does not contain a peptide with this molecular weight, then conventional systems make no identification.

However, the peptide mixture may contain peptides that are related to, but not identical to, the peptides obtained from the database. For example, a peptide may be present in the sample that is chemically related to a peptide in the database. In this case, while the Y and/or B ions may be present, the precursor mwHPlus may not be present. Using embodiments of the present invention, an over abundance of ions at a common retention time (exceeding the detection threshold) provides evidence of a molecule in the sample that is closely related to the sequence of a target precursor. Examples of processes that may give rise to such a situation are modification to the primary protein sequence, or post-translational modification of the protein, or after digestion it may be that one or the other end of the peptide is modified or clipped.

An example of a modified primary protein sequence is a single-nucleotide polymorphism (SNP), which is a difference in a single base in a DNA sequence. SNPs may occur at a frequency of 1 change per 100 bases. In an organism, a SNP can give rise to a tryptic peptide that differs by a single amino acid from a theoretical sequence derived from a protein database. The substitution of a single amino acid is sufficient to change the mass of a precursor relative to the theoretical mass of the unmodified sequence. This substitution leaves the rest of the peptide sequence intact. In particular, up to the point of the amino acid substitution, the Y- and B-ion series of the modified peptide is identical to that of the unmodified sequence.

Thus, a peptide in the sample mixture might occur with substantially the same sequence as the peptide in the database with mwHPlus mass M. But alteration of the sequence or chemical composition of the peptide in the sample will generally change the precursor of mass. Thus a precursor of mass M will not be present in the data, but a significant number of Y or B ions of the sequence corresponding to masses derived from the database are present in the sample data. The ions corresponding to these sub-sequence ions will appear in the data at substantially the same retention time. Thus, hit accumulation does not require that the theoretical mass of the precursor in the database be present in the data.

The retention time of the modified sequence will generally be different than the retention time of the target sequence (if present). The modified and target sequences derive from two distinct peptide molecules, each of which will be retained differently in the chromatographic separation. Thus if the modified and (unmodified) target peptides are both present in the sample, then in the detection chromatogram for the target sequence, two detection peaks, one for each peptide, will appear. The retention times of these detection peaks will reflect the retention times of the respective molecules.

It is worth noting that for the present invention, the mass tolerance of a hit can reflect the inherent mass accuracy of the data. That is, mass tolerance does not need to be widened to take into account possible sequence modifications that affect precursor mass. In the case of a modified sequence, the present invention, which uses a narrow mass tolerance that reflects the inherent mass accuracy of the data, will reject the theoretical precursor mass. But such a narrow mass tolerance will still allow hits to those Y- and B-ions present in the data that correspond to theoretical Y and B masses obtained from the database.

Thus, if sufficient hits accumulate at the retention time of the elution of the modified peptide, then the modified peptide will be detected because matches to the Y- and B-ions alone can produce sufficient hits to detect the presence of the modified peptide in the data. The present invention can detect a modified peptide sequence by using the theoretical fragment masses of the unmodified peptide.

Thus, a search can be carried out and a peptide can be found in the sample data that is related to a peptide in the database. Further more the sample data can provide partial sequence information from the ions that are hit. Thus, a monoisotope of a database peptide may not be present in the LC/MS or LC/MS-E data, but embodiment of the present invention may still identify that the database peptide is present, in possibly modified form, in the sample.

Given the detection of a modified peptide, subsequent investigations of the masses in the data that elute at that detection retention time can reveal the correct sequence and mass of the modified peptide. For example, ab initio sequencing algorithms can be applied to the masses in the data to determine the peptide sequence.

Figure 11:
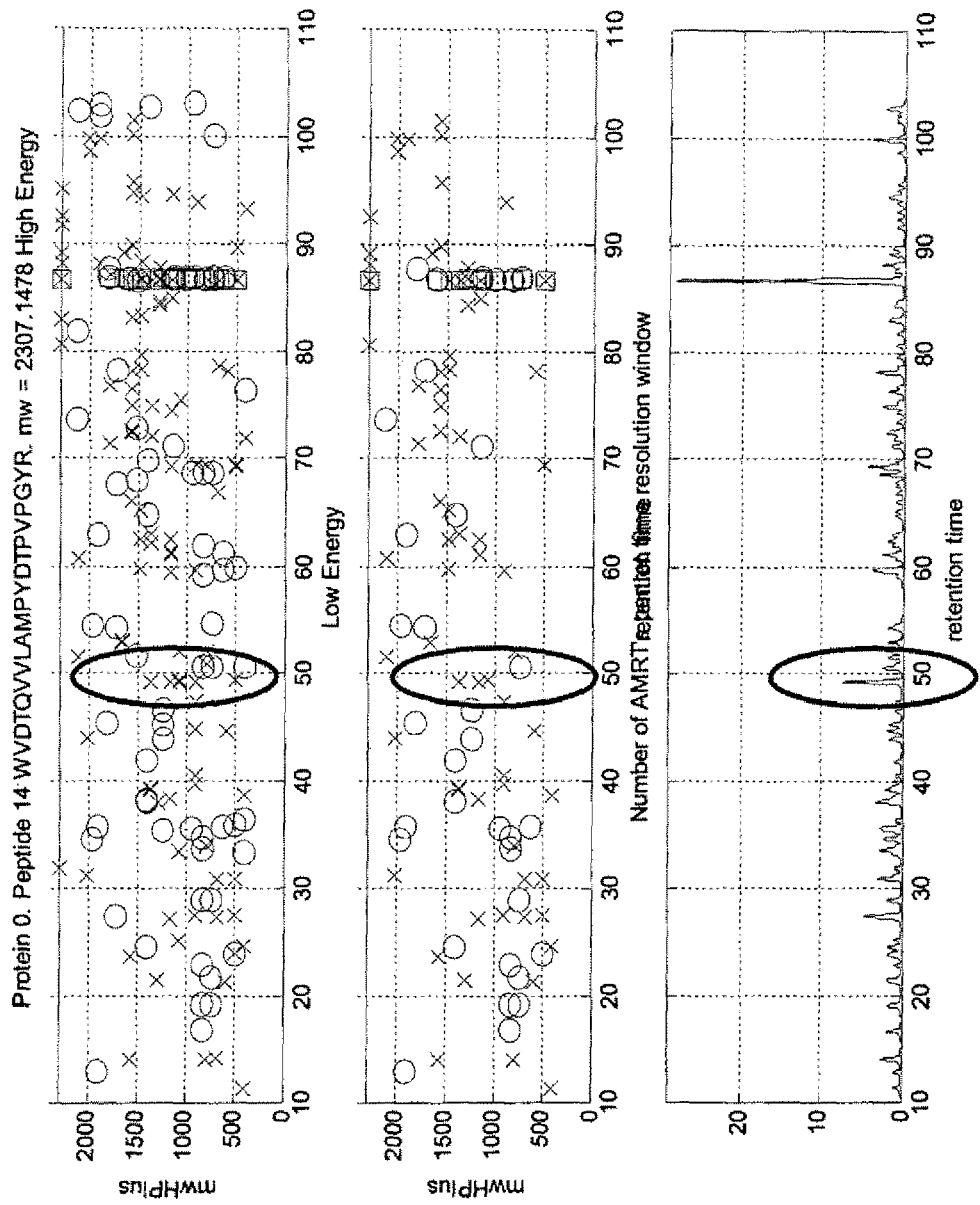
FIG. 11 shows an example of a peptide at approximately 49 minutes that appears to have a significant number of hits, but for which there was no precursor in the database.

FIG. 11 shows, at about 87 minutes, a peptide from the database that is detected to be in the data. The highest value of mwHPlus seen at this retention time is coincident with the mwHPlus of the precursor. FIG. 11 also shows an example of a peptide at approximately 49 minutes that appears to have a significant number of hits (greater than would be expected for noise as it exceeds the threshold), but for which there was no precursor in the database. Specifically, at about 49 minutes, about 5 ions are seen at a common retention time of 49 minutes. No ion is seen with an mwHPlus associated with the peptide. This may be an example of a peptide that is present in the sample and is chemically related to the peptide in the database. Note that the two peptides elute at a different retention times, which indicates a different chemical composition.

Thus, as shown by the plots in FIG. 11, a peptide mixture may contain peptides that are related to, but not identical with, the peptides obtained from the database.

In summary, embodiments of the present invention provide numerous advantages over conventional systems. These include searching the data using a database of known peptide masses. Embodiments of the present invention are able to identify peptide fragments in low energy data (the prior art will assume falsely that each low-energy AMRT is a precursor), without misidentifying low energy fragment as low energy (tryptic) precursor.

Embodiments of the present invention can be configured to perform archival searches of data. As long as the mass resolution of the MS is sufficiently high, and the retention time resolution is sufficiently high, and data is obtained with the high/low switching protocol, peptides should be able to be identified. The intensity and retention time of these peptides can then be measured from the ions in the data that are hit.

Further, embodiments of the present invention enable global searches of data. For example, high energy data can be archived all over the world and search retrospectively with this algorithm.

Embodiments of the present invention are able to detect peptides in data that share sequences with to peptides in database, even when the shared sequence is not identical or the sharing is not complete. For example, the presence of partial Y-ion and B-ion sequences typically are sufficient to identify an AMRT as being related to a peptide from the database.

Further, embodiments of the present invention detect peptides in data that has the same sequence as peptides in database, but are chemically modified. The presence of partial Y-ion and B-ion sequences are sufficient to identify an AMRT as being related to a peptide from the database.

Embodiments of the present invention use retention time alignment in high/low switching MS analysis. Improvements in chromatographic resolution translate directly to improvements in the ability to identify peptides. For example, the detection threshold may be reduced as chromatographic peak width is reduced (resolution increased.) Embodiments of the present invention further use of peak shape and width agreement to tune high/low MS analysis.

Embodiments of the present invention can use retention time specificity to further identify ions that are chemical modifications of precursors, for example, peptides that have lost a neutral water molecule, such as an ammonia molecule. After a peptide is identified as being present in the data, all ions related to that peptide can be identified. As a result, these lower level peptides will not be erroneously identified as precursors or Y or B fragments.

Embodiments of the present invention provide measurement of background noise. As a result, the significance or confidence of identification can be calculated based upon statistical behavior of data. Rather than histogram the number of hits in a retention time interval, the detection chromatogram can count only the longest contiguous sequence of hits within a retention time interval. That is, if Y2, Y4, Y5, Y6, Y7, Y10 are hit, then only four these ions (Y4, Y5, Y6, Y7) form a contiguous sequence of Y ions. The detection histogram would contain 4 at the retention time of the ions. The significance of a detection threshold can be evaluated by monte-carlo means, or by obtaining the statistical properties of background hits from the data. Further, embodiments of the present invention can be configured to use distributions of peptide in database to assess significance of hits Embodiments of the present invention can also be configured to use intensity and sequence rules in the database search. For example, if a candidate precursor AMRT is seen in both high and low-energy spectra, the intensity of the precursor at high-energy spectra can be compared with the intensity of the precursor seen in the low-energy spectra. For the AMRT to be a precursor, its intensity at high-energy must be less than that at low-energy. If the intensity at high-energy is measured to be greater than that at low-energy, it is likely the AMRT seen in low- and high-energy are in fact fragments of yet another precursor. In this case, the PDS algorithm can be configured to reject the low-energy AMRT as a possible precursor, thereby removing possible false-positive identification.

As an example of another rule, hits to a given precursor may be eliminated if the intensity of a fragment AMRT is judged to be an outlier with respect to the intensities of other fragment ARMTs possibly associated with that precursor.

As an example of another rule, it may be that for certain precursor sequences, the amino acid composition indicates that certain Y or B ions of that precursor should ionize efficiently. If the relative or absolute intensities of fragment AMRTs are inconsistent with such a model of ionization efficiency, than that inconsistency may provide grounds to reject the identification of the sequence. On the other hand, if the relative or absolute intensities of fragment AMRTs are consistent with such models of ionization efficiency, than that may confirm the identification of the sequence.

A problem with analyzing AMRTs is their dynamic range of intensities. AMRTs in a set of data can occur with intensities that span a large dynamic range. The dynamic range of intensities can be more than 1:1000. Advances in MS technology may extend this dynamic range to 1:10,000 or more. The large dynamic range arises from two effects. First, a given protein in the sample may produce AMRTs whose dynamic range may be 1:100 or more, as variations in the composition of peptides give rise to variations in ionization efficiency. As a result, some AMRTs may ionize more efficiently than others. Second, different proteins can occur in a sample with large dynamic range of concentration.

Thus, low-intensity AMRTs may be generated from multiple sources. For example, low intensity AMRTs can be generated from high concentration proteins whose peptides have ionize poorly or from low concentration proteins whose peptides ionize efficiently.

Thus, the large dynamic range in intensity is a potential source of false positive identifications. AMRTs or ions from a high concentration protein that are poorly ionizing might be falsely interpreted as arising from a highly ionizing peptide from a low concentration protein.

A method is disclosed for handling the complexity caused by dynamic range. The technique, which has been termed the Electronic Depletion Algorithm (EDA) identifies and removes all ions associated with high concentration proteins, before the low-concentration proteins are analyzed. Removing AMRTs associated with high concentration proteins removes all the high intensities AMRTs in the sample as well as all the low intensity ions in the sample that come from the high concentration proteins. Consequently, low-intensity AMRTs from high concentration proteins will not be confused with AMRTs from low-concentration proteins that ionize efficiently.

Removing the low intensity AMRTs and ions associated with high concentration proteins reduces an important source of false positives. For example variations in a low-intensity AMRT may erroneously be interpreted as evidence of a biomarker of a low-concentration protein; where, in fact, it is a misidentified, poorly ionizing fragment of a high-concentration protein.

Figure 12:
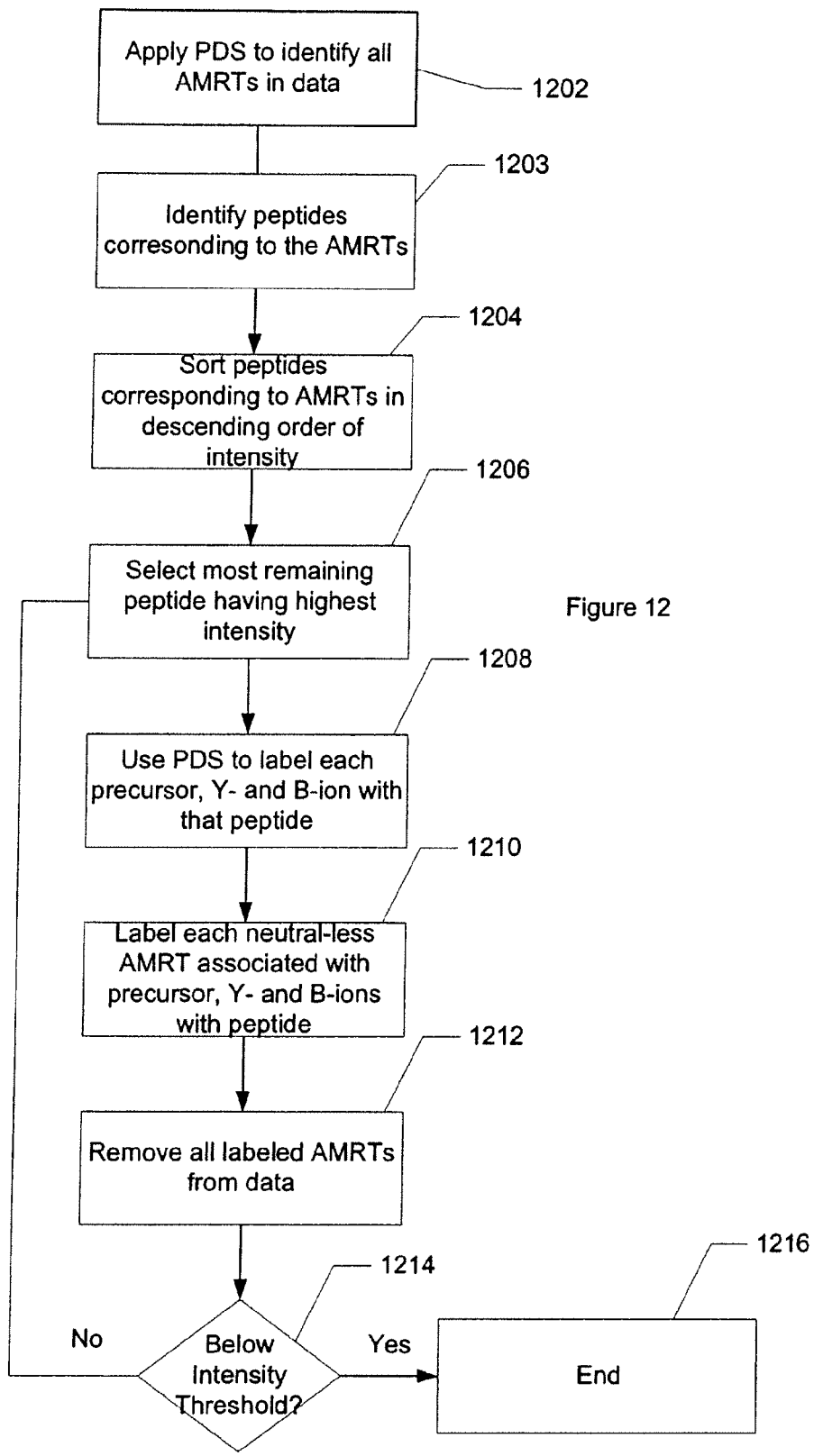
FIG. 12 is a flow chart for a method for performing the electronic depletion algorithm (EDA) according to an embodiment of the present invention.

FIG. 12 is a flow chart for a method for performing EDA according to an embodiment of the present invention. In step 1202, all AMRTs in the data are identified using the PDS described above. The peptides corresponding to the AMRTs are identified in step 1203. The identified AMRTs are sorted in intensity from most intense to least intense in step 1204 and stored in a list.

In step 1206, the most intense peptide remaining in the list (the top item in the list) is selected. Using the PDS, each precursor, Y- and B-ion associated with that peptide is labeled with the peptide in step 1208. In step 1210 each neutral-loss AMRT associated with the precursors, Y- and B-ions labeled in step 1208 is labeled with the peptide. In step 1212, all labeled AMRTs are removed from the data. If there are no AMRTs having intensity higher than a pre-determined intensity threshold as determined in step 1214, the method ends in step 1216. If, on the other hand, there exists another AMRT having intensity higher than the intensity threshold, processing continues in step 1206 using the remaining peptide with the highest intensity.

Embodiments of the present invention can be configured to measure standard error in retention time and in mwHPlus. The measurement error in retention time that is relevant to this method is the error of the AMRTs and ions that are common to a single peptide. Thus the error is not an elution error. The error is due only to the limitations with which we can measure retention time.

The measurement error in mwHPlus that is relevant to embodiments of the present invention is the error relative to a database of accurately mass-measured proteins and peptides. The error is due to the limitations with which m/z can be measured in a mass spectrometer. This error in m/z has two sources, which are statistical noise and calibration error.

Retention time and mwHPlus error must be estimated because these errors are used to set the thresholds used in determining which AMRTs constitute a hit and possibly in configuring the detection chromatogram in the PDS method described above.

Retention time error and mwHPlus error are measured as a standard deviation of an error distribution. Given the standard deviations, the thresholds used in determined which AMRTs constitute a hit and which are have a significant number of hits in the detection chromatogram are then some multiple of the standard deviation. Typical values might be 3 for a false-positive rate of 3 sigma or 1 in 1000, or 6 sigma, specifying a formal false positive rate of 1 in $10^6$.

According to one embodiment of the present invention, to determine retention time error and mwHPlus error, ions that are common in low and in high energy are identified. For example, a tryptic precursor that appears in low energy will also appear in high energy, albeit at reduced intensity. The nominal difference in retention time between the ions is perforce zero. The nominal difference in mwHPlus is zero.

The observed retention time difference between these ions is a measure of the error in retention time. The standard deviation of this error, as determined by combining errors from many such pairs, is the basis of the measurement of the standard error in retention time.

Figure 13:
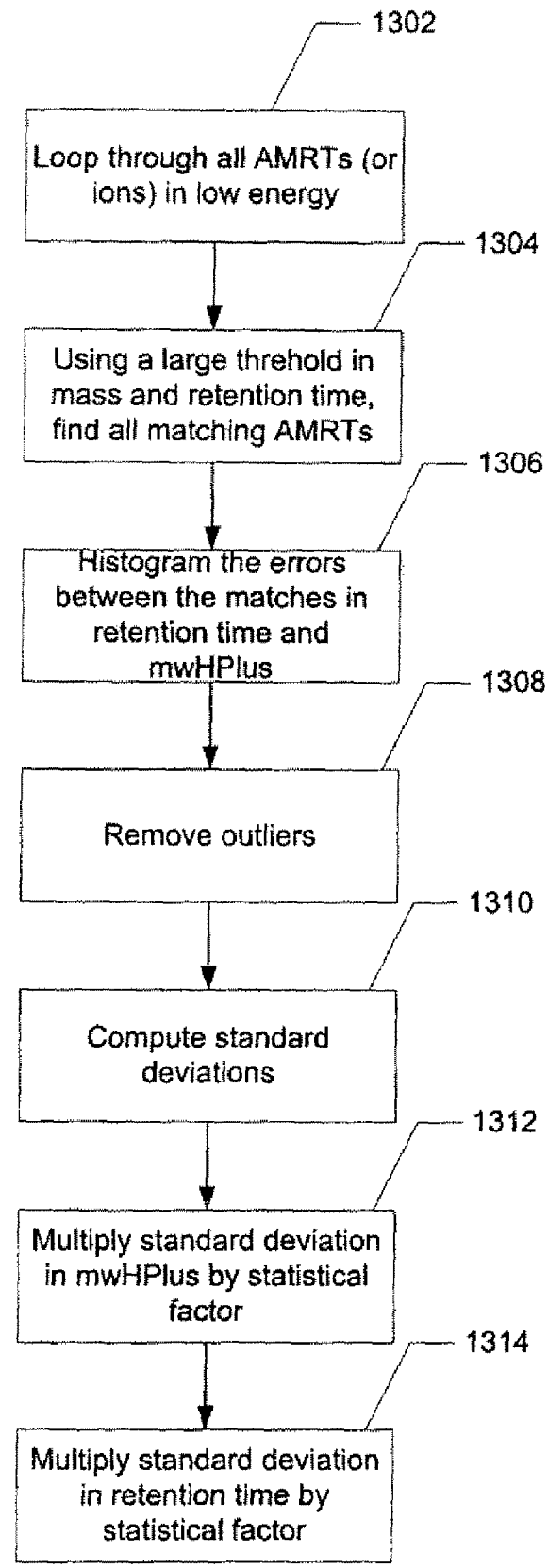
FIG. 13 is a method for determining retention time error and mwHPlus error according to an embodiment of the present invention.

Based on the foregoing, FIG. 13 is a method for determining retention time error and mwHPlus error according to an embodiment of the present invention. In step 1302, loop through all AMRTS (or ions) in low energy. Using a large threshold in mass and retention time (e.g., 50 ppm and 0.5 minutes, respectively) find all AMRTs (or ions) in high energy that match in step 1304. In step 1306 the errors between matches in retention time and mwHPlus are analyzed. In step 1308, outliers are removed using standard techniques such as median filtering. In step 1310, the standard deviations for the resulting distributions are computed. In step 1312, the standard deviation in mwHPlus is multiplied by a statistical factor (between 3 and 6) to establish a molecular weight threshold that can be used in determining which AMRTs hit in the PDS algorithm. In step 1314, the standard deviation in retention time is multiplied by a statistical factor (between 3 and 6) to establish a retention time threshold that can be used in step generating the detection chromatogram of the PDS algorithm The detection threshold used for determining whether a peptide is in the data or not can be determined in the following manner. A peptide in the database is considered detected in the data if there are more than N AMRTs (or ions) found. The number N depends on the complexity of the sample. The more complex the sample the higher must be N. N can be empirically determined from the data by examining the background of hits. A standard histogram technique or other statistical technique can be employed to establish N. In practice, a value of N between 4 and 6, inclusive has been found to be an acceptable detection threshold for AMRTs found in high/low data.

The results obtained from the invention are lists of peptides identified in a sample. Each such peptide in the list contains the peptide sequence from the database, and the measured retention time, measured and theoretical mass of the precursor, the measured intensity of the precursor, as well as the measured retention times, intensities and masses of the fragment ions found in the data and associated with the precursor. It is anticipated that these results will have great utility in the field of proteomics. For example, four such proteomic applications are: identification of proteins in a sample, retention time tracking of peptides between samples, and quantitation of peptides and proteins between samples.

A peptide that is identified by this method gives evidence that the originating protein sequence occurred in the sample. For example, the list of proteins corresponding to the tryptic peptides identified by the present invention is one method for identifying proteins present in the sample. From the identity and concentration of the observed peptides, algorithms known in the art can also infer the identity and the concentration of the parent proteins.

The entrants on this list may contain false positives. That is, false identifications of peptides may give rise to false identification of proteins. The reduction or elimination of false positives can be accomplished by one of several means known in the prior art. One can require that for a protein to be identified more than one peptide to that protein be identified by the method of the current invention. The user may specify that N>1 such peptides be detected. Alternatively, the user may specify that a minimum percentage coverage (by amino acid) of protein sequence be achieved by the detection of 1 or more peptides to that protein. In addition, a user may require that the protein be identified in each of several replicate LC/MS analyses of the sample. Other possible rules, known in the art, may be applied to reduce false positive identification of proteins.

The present invention can be applied to the data obtained multiple samples analyzed on the same or different LC/MS systems. If a peptide sequence from a database is seen in more than one such sample or analysis, then the retention times of that peptide from each sample or analysis can be compared. Thus the invention provides a means of tracking the retention time of a peptide from injection to injections. In addition, the peptide could be detected in data obtained by different instruments employing different LC separation methodologies. Thus the retention time of that peptide could be compared between different such instruments and LC separations.

The consistency of retention times of the same sequence as seen in multiple injections on the same or different instruments can be checked. Such consistency checking can be used to detect and to eliminate false positive identifications.

Given the intensities of the same peptide as seen in replicate injections of a given mixture, or as seen in injections of a sample under different conditions, methods of the prior art can be applied to calibrate intensities and to determine expression changes in peptide and proteins. For example, if the same peptide sequence is detected between injections of two samples, the ratios of intensities of the corresponding precursors could be computed. If these peptides are from a calibration standard protein, then the ratio allows for the relative or absolute concentration calibration of the respective injections. If the peptides are from proteins endogenous to the sample, then the ratio can be used to determine the expression level change of the peptide or to the originating protein.

The method of the current invention can be applied to mixtures other than that of peptides. Given (1) any mixture of molecules and (2) a database containing the masses of those molecules and their fragments, the method can be used to identify the molecules in the sample.

For the method to be applied, the sample is be analyzed by the LC/MS systems described about. The precursor molecules fragment by the methods described above, and the theoretical masses of the precursor and fragments are be known. If these conditions are met, then the precursors can be identified by the method of the present invention. In the above discussion of the method, the precursor then refers to mass of the ion any seen at low-energy. The fragment then refers to the mass of any fragment of the precursor seen in high-energy, or possibly in low-energy. The method then identifies the originating molecule that is separated in the column.

Thus, for example, metabolic studies can benefit from the present invention. The step of digestion is not needed for molecules of metabolism. All that is needed for the present invention are a list of exact, theoretical masses corresponding to the precursor and its associated fragments. With such a list, the method can detect the presence of that set or subset of masses and the retention time at which the originating, precursor molecule eluted from the chromatographic column.

In a preferred embodiment, the PDS algorithm and EDA algorithm is applied to data acquired by spectra collected in alternating high-energy and low-energy modes. However both of these algorithms can be applied to spectra collected in only one mode, i.e., a fixed-energy mode. Thus, for example, these algorithms can be applied either to the low-energy spectra or to the high-energy spectra alone. That is, in principle, both modes could be collected, but peptides can be identified via the use of the PDS or EDA algorithms applied only to a single mode. As long as some fragmentation of a precursor ion occurs within a single-energy mode, then the application of these algorithms will detect the presence of the precursor and/or its fragments in the data. The in-source fragmentation evident in FIGS. 5C and 11C shows that the PDS or EDA algorithms could be applied to low-energy data alone.

Thus, the requirement that data be collected in two modes is preferred, though not necessary for the application of the PDS or EDA algorithms.

It should also be noted that the PDS or EDA algorithms can be applied to spectral data intentionally acquired only at a single, fixed-energy. In fact it may be advantageous to adjust the voltage (or voltage steps) in a fixed-energy mode to correspond to a voltage that is intermediate in value between that typically used for low-energy or high-energy acquisition. The intent would be to collect spectra that contain an optimum mix of precursors and fragments. Such acquisition would also lend itself to the identification of peptides via use of the PDS or EDA algorithms.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for identifying proteins in a mixture comprising:
   receiving a first set of mass and retention time information associated with precursors and a second set of mass and retention time information associated with fragments of the precursors, wherein said first set of mass and retention time information and said second set of mass and retention time information are obtained from an LC/MS experiment using the mixture;
   selecting a target peptide;
   determining, for the target peptide, a target precursor and corresponding Y and B fragment ions of the target precursor, wherein the target precursor and said corresponding Y and B fragment ions of the target precursor have associated masses;
   determining mass matches for a substantially same retention time in said first set of mass and retention time information and said second set of mass and retention time information in accordance with the masses of said target precursor and said corresponding Y and B fragment ions of the target precursor; and
   identifying, in accordance with said mass matches for a substantially same retention time, whether the target peptide is present in the mixture.

2. The method of claim 1, wherein the target peptide is selected from a database.

3. The method of claim 1, wherein the mass matches are determined in accordance with a search tolerance.

4. The method of claim 3, wherein the search tolerance is user specified.

5. The method of claim 3, wherein the search tolerance is automatically determined from data using statistics.

6. The method of claim 1, wherein a mass match is determined if any of said target precursor and said corresponding Y and B fragment ions of the target precursor have a corresponding mass in any of said first set of mass and retention time information and said second set of mass and retention time information.

7. The method of claim 1, wherein a detection chromatogram is created.

8. The method of claim 7, wherein the detection chromatogram identifies a number of ions within each of a plurality of retention time intervals.

9. The method of claim 7, wherein the detection chromatogram is derived using Gaussian shaped peaks.

10. The method of claim 1, wherein the first set of mass and retention time information is obtained as a result of applying a low energy mode in a mass spectrometer and the second set of mass and retention time information is obtained as a result of applying a high energy mode in a mass spectrometer to fragment the precursors.

11. The method of claim 1, further comprising:
    determining a detection threshold; and
    identifying whether a peptide is present based on whether a count of mass matches in a particular retention time interval exceeds the detection threshold.

12. The method of claim 11, further comprising:
    estimating a noise floor associated with the detection threshold; and
    analyzing a significance of a peptide identification based on the count and the estimate of the noise floor.

13. The method of claim 11, wherein the target peptide is identified as being in the mixture in accordance with a count based on matches to said corresponding Y and B fragment ions of the target precursor without a match to said target precursor.

14. The method of claim 11, wherein said detection threshold varies with a complexity of the mixture.

15. A method for identifying proteins in a mixture comprising:
    receiving mass and retention time information associated with one or more precursors and one or more fragments of the one or more precursors, wherein said mass and retention time information are obtained from an LC/MS experiment using the mixture when operating a mass spectrometer in a single fixed energy mode;
    selecting a target peptide;
    determining, for the target peptide, a target precursor and corresponding Y and B fragment ions of the target precursor, wherein the target precursor and said corresponding Y and B fragment ions of the target precursor have associated masses;
    determining mass matches for a substantially same retention time in said mass and retention time information in accordance with the masses of said target precursor and said corresponding Y and B fragment ions of the target precursor; and
    identifying, in accordance with said mass matches for a substantially same retention time, whether the target peptide is present in the mixture.

16. The method of claim 15, wherein said single fixed energy mode corresponds to a voltage having an intermediate value with respect to a first voltage when operating in a low energy mode and a second voltage when operating in a high energy mode for fragmenting precursors.

17. A system comprising:
    a liquid chromatograph to which the mixture is applied to separate the mixture producing a separated mixture;

a mass spectrometer that measures masses in the separated mixture;

a database from which a target peptide is selected;

a computer coupled to the database and an output of the mass spectrometer, said computer having code executing thereon which, when executed, causes the computer to:

receive a first set of mass and retention time information associated with precursors and a second set of mass and retention time information associated with fragments of the precursors, wherein said first set of mass and retention time information and said second set of mass and retention time information are obtained from an LC/MS experiment using the mixture;

select a target peptide;

determine, for the target peptide, a target precursor and corresponding Y and B fragment ions of the target precursor, wherein the target precursor and said corresponding Y and B fragment ions of the target precursor have associated masses;

determine mass matches for a substantially same retention time in said first set of mass and retention time information and said second set of mass and retention time information in accordance with the masses of said target precursor and said corresponding Y and B fragment ions of the target precursor; and identify, in accordance with said mass matches for a substantially same retention time, whether the target peptide is present in the mixture.

18. The system of claim 17, wherein identifying whether the target peptide is present in the mixture includes consideration of mass matches for fragments at peptide bonds other than those associated with said corresponding Y and B fragment ions.

19. The system of claim 17, wherein the mass matches are determined in accordance with a search tolerance.

20. The system of claim 17, wherein a mass match is determined if any of said target precursor and said corresponding Y and B fragment ions of the target precursor have a corresponding mass in any of said first set of mass and retention time information and said second set of mass and retention time information.

* * * * *